United States Patent [19]

Sanz et al.

[11] Patent Number: 5,185,346
[45] Date of Patent: Feb. 9, 1993

[54] (1H-AZOL-1-YLMETHYL)SUBSTITUTED QUINOLINE DERIVATIVES

[75] Inventors: Gerard C. Sanz, Garges les Gonesse; Marc G. Venet, Paris, both of France; Eddy J. E. Freyne, Rumst; Alfons H. M. Raeymaekers, Beerse, both of Belgium

[73] Assignee: Hanssen Pharmaceutica, Beerse, Belgium

[21] Appl. No.: 704,746

[22] Filed: May 23, 1991

Related U.S. Application Data

[63] Continuation-in-part of Ser. No. 434,205, Nov. 13, 1989, abandoned.

[30] Foreign Application Priority Data

Nov. 29, 1988 [GB] United Kingdom ............... 8827821

[51] Int. Cl.$^5$ .................. C07D 401/06; A61K 31/47
[52] U.S. Cl. ................................ 514/312; 546/157; 546/156; 548/335.1; 548/313.7; 548/346.1; 548/344.1; 548/315.1; 548/315.4
[58] Field of Search ............... 546/157, 156; 514/312

[56] References Cited

U.S. PATENT DOCUMENTS

| 4,410,539 | 10/1981 | Cross et al. | 546/157 |
| 4,792,561 | 12/1988 | Walker et al. | 546/157 |
| 4,859,684 | 8/1989 | Raeymaekers et al. | 514/314 |

OTHER PUBLICATIONS

Bell et al., *J. Med. Chem.*, 1989, 32, 1552–1558–2(1-H)-Quinolinones with Cardiac Stimulant Activity. 3. Synthesis and Biological Properties of 6-Imidazol-1-yl Derivatives.

leclerc et al., *J. Med. Chem.* 1986, 29, 2427–2432–Cardiotonic Agents. 1. Synthesis and Structure-Activity Relationships in a New Class of 3-, 4-, and 5-Pyridyl-2(1H)-quinolone Der's.

Alabaster et al., *J. Med. Chem.* 1988, 31, 2048–2056–2(1-H)-Quinolinones with Cardiac Stimulant Activity. 1. Synthesis and Biological Activities of (Six–Membered Heteraryl)-Substituted Derivs.

*Primary Examiner*—Robert T. Bond
*Assistant Examiner*—E. C. Ward
*Attorney, Agent, or Firm*—Charles J. Metz

[57] ABSTRACT (1H-azol-1-ylmethyl)substituted quinoline derivatives, compositions containing the same, and methods of treating mammals suffering from disorders which are characterized by an increase proliferation and/or abnormal differentation of epithelial tissues.

18 Claims, No Drawings

(1H-AZOL-1-YLMETHYL)SUBSTITUTED QUINOLINE DERIVATIVES

CROSS-REFERENCE TO RELATED APPLICATION

This is a continuation-in-part of U.S. Ser. No. 434,205, filed Nov. 13, 1989 now abandoned.

BACKGROUND OF THE INVENTION

In U.S. Pat. No. 4,859,684 there are described (1H-azol-1-ylmethyl) substituted benzimidazole derivatives which compounds are useful as androgenic hormone biosynthesis inhibitors. The compounds of the present invention differ from the cited art compounds by the fact that they contain a quinoline or quinolinone moiety in place of an benzimidazole moiety. U.S. Pat. No. 4,792,561 discloses carbostyril derivatives having combined thromboxane synthetase and cyclic-AMP phosphodiesterase inhibiting properties. Some compounds of the latter patent and the novel compounds of the present invention have now been found to suppress the plasma elimination of retinoic acids. Further, some of said compounds also inhibit the formation of androgens from progestines and/or inhibit the action of the enzyme complex aromatase which catalyses the formation of estrogens from androgenic steroids in mammals.

DESCRIPTION OF THE INVENTION

The present invention is concerned with compounds of formula:

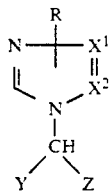
(I)

the pharmaceutically acceptable acid addition salts thereof and stereochemically isomeric forms thereof, wherein:

—$X^1$=$X^2$— represents a bivalent radical of formula

—CH=CH— (x),

—CH=N— (y), or

—N=CH— (z);

R represents hydrogen or $C_{1-6}$alkyl;

Y represents hydrogen, $C_{1-10}$alkyl, $C_{3-7}$cycloalkyl, $Ar^1$, $Ar^2$—$C_{1-6}$alkyl, $C_{2-6}$alkenyl or $C_{2-6}$alkynyl; and Z represents a radical of formula

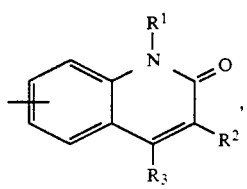
(a-1)

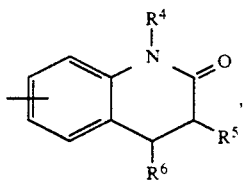
(a-2)

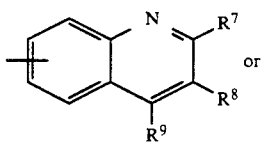
(a-3)

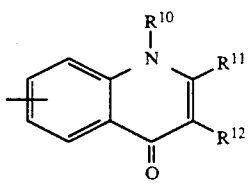
(a-4)

wherein $R^1$, $R^4$ and $R^{10}$ each independently represent hydrogen, $C_{1-6}$alkyl or $Ar^2$—$C_{1-6}$alkyl;

$R^2$, $R^5$, $R^8$ and $R^{12}$ each independently represent hydrogen, $C_{1-6}$alkyl or $Ar^2$;

$R^3$, $R^6$ and $R^{11}$ each independently represent hydrogen or $C_{1-6}$alkyl; and $R^7$ and $R^9$ each independently represent hydrogen, $C_{1-6}$alkyl, $C_{1-6}$alkyloxy, halo, amino, or mono or di-($C_{1-6}$alkyl)amino; wherein in the foregoing:

$Ar^1$ represents phenyl, substituted phenyl, naphthalenyl, pyridinyl, imidazolyl, triazolyl, thienyl, furanyl or thiazolyl and $Ar^2$ represents phenyl or substituted phenyl; wherein said substituted phenyl in $Ar^1$ or $Ar^2$ represents phenyl substituted with 1,2 or 3 substituents each independently selected from the group consisting of halo, hydroxy, trifluoromethyl, $C_{1-6}$alkyl, $C_{1-6}$alkyloxy, cyano, amino, mono-and di($C_{1-6}$alkyl)amino, nitro, carboxyl, formyl and $C_{1-6}$alkyloxycarbonyl.

Novel compounds within the present invention are those compounds of formula (I) as defined hereinabove, provided that when (1)—$X^1$=$X^2$— represents bivalent radical of formula —CH=CH—, (2) R represents hydrogen, (3) Z represents a radical of formula (a-1) or (a-2), and (4) $R^1$, $R^2$, $R^3$, $R^4$, $R^5$ and $R^6$ all represent hydrogen, then Y is other than hydrogen, $C_{1-10}$alkyl, $Ar^1$ or $Ar^2$—$C_{1-6}$alkyl, As used in the foregoing definitions the term halo is generic to fluoro, chloro, bromo and iodo; the term "$C_{1-6}$alkyl" defines straight and branched chain, saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$alkyl" defines the higher homologs of "$C_{1-6}$alkyl" containing 1-10 carbon atoms; the term "$C_{3-7}$cycloalkyl" is generic to cyclopropyl, cyclobutyl, cyclopentyl, cyclohexyl and cycloheptyl; "$C_{2-6}$alkenyl" defines straight and branched chain hydrocarbon radicals containing one double bond having from 2 to 6 carbon atoms such as, for example, ethenyl, 2-propenyl, 3-butenyl, 2-butenyl, 2-pentenyl, 3-pentenyl, 3-methyl-2-butenyl and the like; "$C_{2-6}$alkynyl" defines straight and branched chain hydrocarbon radicals containing one triple bond and having 2 to 6 carbon atoms such as, for example, 2-propynyl,2-butynyl,3-butynyl,2-pentynyl, 3-pentynyl, 4-pentynyl and the like.

It is to be understood that the

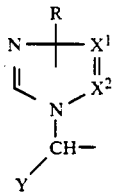

moiety hereinafter referred as the 1H-azol-1-ylmethyl moiety may be substituted on either the 5, 6, 7 or 8 position of the bicyclic ring system, the 6 or 7 position being preferred, the 6 position being most preferred.

Further it should be noted that the compounds of formula (I) wherein Z is a radical of formula (a-1) are denoted as compounds of formula (I-a-1), compounds of formula (a-2) are denoted as compounds of formula (I-a-2), compounds of formula (a-3) are denoted as compounds of formula (I-a-3) and compounds of formula (a-4) are denoted as compounds of formula (I-a-4).

The acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

From formula (I) it is evident that the compounds of this invention may have several asymmetric carbon atoms in their structure. Pure isomeric forms of the compounds of formula (I) can be separated from the mixture by conventional separation methods. Preferably, if a specific stereoisomer is desired, said compounds will be synthesized by stereoselective methods of preparation. These methods will advantageously employ enantiomerically pure starting materials.

Further it is evident that the compounds of formula (I) may also contain in their structure a tautomeric system and consequently these compounds can be present in each of their tautomeric forms.

Particular compounds of the present invention are those compounds of formula (I) wherein R is hydrogen; and/or Y is hydrogen, $C_{1-6}$alkyl, $C_{3-7}$ cycloalkyl, phenyl, substituted phenyl, pyridinyl, imidazolyl or thienyl; and/or Z is a radical of formula (a-1), (a-2), (a-3) or (a-4) wherein $R^1$, $R^2$, $R^3R^4$, $R^5$, $R^6$, $R^8$, $R^{10}$, $R^{11}$ and $R^{12}$ each independently are hydrogen or $C_{1-4}$alkyl, and $R^7$ and $R^9$ each independently are hydrogen, $C_{1-4}$alkyl, $C_{1-4}$alkyloxy or halo.

More particular compounds are those particular compounds wherein —$X^1$=$X^2$— is a radical having the formula (x) or (y); and Y is hydrogen, $C_{1-4}$alkyl, cyclopropyl, cyclopentyl, cyclohexyl, imidazolyl, pyridinyl, thienyl or phenyl optionally substituted with one or two substituents each independently selected from halo, $C_{1-4}$alkyl, $C_{1-4}$alkyloxy and trifluoromethyl.

Among the compounds of the aforementioned subgroups special emphases is put on compounds of formula (I) wherein Z is a radical of formula (a-1) wherein $R^1$ and $R^2$ are hydrogen, $R^3$ is hydrogen or $C_{1-4}$alkyl and Y is hydrogen, $C_{1-4}$alkyl or phenyl optionally substituted with one or two halo atoms; and compounds of formula (I) wherein Z is a radical of formula (a-2) wherein $R^4$, $R^5$ and $R^6$ all being hydrogen, and Y is hydrogen, $C_{1-4}$alkyl, cyclopropyl or phenyl optionally substituted with one or two halo atoms; and compounds of formula (I) wherein Z is a radical of formula (a-3) wherein $R^7$ is hydrogen, halo, or $C_{1-4}$alkyloxy, $R^8$ is hydrogen, $R^9$ is hydrogen, $C_{1-4}$alkyl or $C_{1-4}$alkyloxy and Y is hydrogen, $C_{1-4}$alkyl, cyclopropyl, cyclohexyl, imidazolyl, thienyl or phenyl optionally substituted with one or two substituents each independently selected from halo, $C_{1-4}$alkyl, $C_{1-4}$alkyloxy and trifluoromethyl; and compounds of formula (I) wherein Z is radical having the formula (a-4) wherein $R^{10}$ and $R^{12}$ are hydrogen, $R^{11}$ is $C_{1-4}$alkyl and Y is hydrogen.

Preferred compounds of formula (I) wherein Z is a radical of formula (a-1) are those compounds wherein R is hydrogen; —$X^1$=$X^2$— is a radical of formula (x) or (y); Y is isopropyl, phenyl or halophenyl; $R^1$ and $R^2$ are both hydrogen; and $R^3$ is methyl.

Most preferred compounds of formula (I) wherein Z is a radical of formula (a-1) are selected from 6-[(4-fluorophenyl)(1H-imidazol-1-yl)methyl]-2(1H)-quinolinone, the pharmaceutically acid addition salts and possible sterioisomeric forms thereof.

Preferred compounds of formula (I) wherein Z is a radical of formula (a-2) are those compounds wherein R is hydrogen; —$X^1$=$X^2$— is a radical of formula (x) or (y); Y is cyclopropyl, phenyl or halophenyl and $R^4$, $R^5$ and $R^6$ are all hydrogen.

Most preferred compounds of formula (I) wherein Z is a radical of formula (a-2) are selected from 6-[(3-chlorophenyl)(1H-imidazol-1-yl)methyl]-3,4-dihydro-2(1H)-quinolinone and 3,4-dihydro-6-[(1H-imidazol-1-yl)phenylmethyl]-2(1H)-quinolinone, the pharmaceutically acceptable acid addition salts and possible stereoisomers thereof.

Preferred compounds of formula (I) wherein Z is a radical of formula (a-3) are those compounds wherein R is hydrogen; —$X^1$=$X^2$— is a radical of formula (x) or (y); Y is phenyl, halophenyl, dihalophenyl, methoxyphenyl or cyclohexyl.

Most preferred compounds of formula (I) wherein Z is a radical of formula (a-3) are selected from 6-[(1H-1,2,4-triazol-1-yl)[3-(trifluoromethyl)phenyl]methyl]-quinoline, the pharmaceutically acceptable acid addition salts and possible stereoisomers thereof.

The compounds of formula (I) can be prepared by N-alkylating an azole of formula (II) or an alkali metal salt thereof with a quinoline or quinolinone derivative of formula (III).

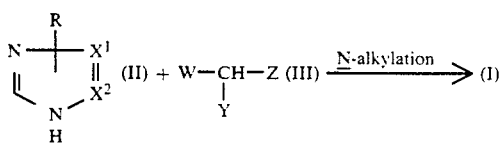

In formula (III) W represents an appropriate reactive leaving group such as, for example, halo, e.g., fluoro, chloro, bromo, iodo or a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

The above described N-alkylation is conveniently carried out by stirring the reactants in the presence of a suitable solvent such as, for example, an aromatic hydrocarbon, e.g. benzene, methylbenzene, dimethylbenzene, and the like; an ester, e.g. ethyl acetate, γ-butyrolacetone and the like; a ketone, e.g. 2-propanone, 4-methyl-2-pentanone and the like; an ether, e.g. 1,4-dioxane, 1,1'-oxybisethane, tetrahydrofuran and the like; a polar aprotic solvent, e.g. N,N-dimethylformamide, N,N-dimethylacetamide, dimethyl sulfoxide, 1-methyl-2-pyrrolidinone, acetonitrile, hexamethylphosphor triamide, 1,3-dimethyl-3,4,5,6-tetrahydro-2(1H)-pyrimidinone, 1,3-dimethyl-2-imidazolidinone, benzonitrile and the like; or a mixture of such solvents. Somewhat elevated temperatures may be appropriate to enhance the rate of the reaction and in some cases the reaction may even be carried out at the reflux temperature of the reaction mixture. The addition of an appropriate base such as, for example, an alkali or an earth alkaline metal carbonate, hydrogen carbonate, hydroxide, amide or hydride, e.g. sodium hydroxide, potassium hydroxide, potassium carbonate, sodium hydride and the like or an organic base, such as, for example, N,N-dimethyl-4-pyridinamine, pyridine, N,N-diethylethanamine or N-(1-methylethyl)-2-propanamine may be employed to pick up the acid which is liberated during the course of the reaction. In some instances it may be advantageous to use an excess of the azole (II) or to convert the azole first into a suitable salt form thereof such as, for example, an alkali or earth alkaline metal salt, by reacting (II) with an appropriate base as defined hereinabove and subsequently using said slat form in the reaction with the alkylating reagent of formula (III). Additionally, it may be advantageous to conduct said N-alkylation reaction under an inert atmosphere such as, for example, oxygen-free argon or nitrogen gas. Said alkylation may also be carried out by applying art-known conditions of phase transfer catalysis reactions.

Compounds of formula (I) wherein $-X^1=X^2-$ is a bivalent radical of formula (x), said compounds being represented by formula (I-x), may also be prepared by reacting a quinoline of formula (III) with a 1-protected imidazole of formula (II-x) following the N-alkylation procedures described hereinabove for the preparation of compounds of formula (I) starting from (II) and (III).

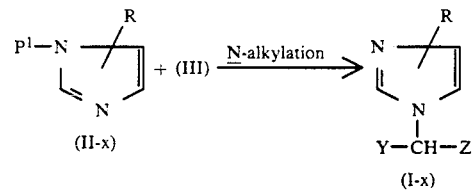

In (II-x) $P^1$ represents a protective group such as, for example, $C_{1-6}$alkylcarbonyl, $C_{1-6}$alkyloxycarbonyl, arylcarbonyl or a tri($C_{1-6}$alkyl)silyl group. In some instances the reaction of (II-x) with (III) first yields a 1-protected imidazolium salt of formula (IV) which may in situ, or if desired, after isolating and further purifying it, be deprotected by stirring it in an aqueous basic or acidic solution.

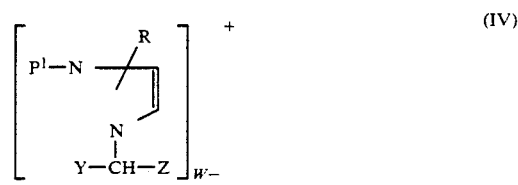

In (IV) $W^-$ is an anion arising from an acid such as, for example hydrochloric acid, hydroboromic acid, methanesulfonic acid, 4-methylbenzenesulfonic acid and the like acids.

Compounds of formula (I) wherein $-X^1=X^2-$ is a bivalent radical of formula (y), said compounds being represented by formula (I-y), can also be prepared by endoN-alkylation of a triazolamine of formula (II-y) with a quinoline of formula (III) and subsequent deamination of the thus prepared triazolium salt, wherein $W^-$ is an anion as defined hereinabove.

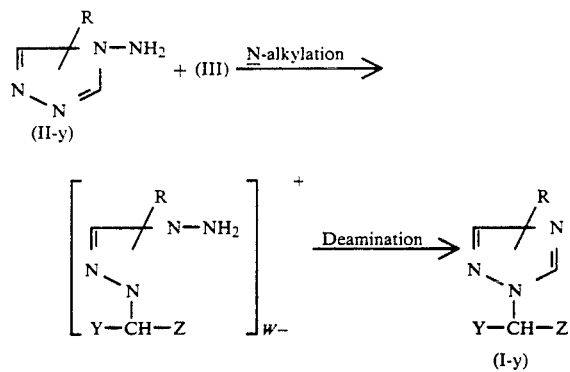

The endo-N-alkylation reaction of (II-y) with (III) is carried out according to similar procedures as described hereinabove for the preparation of a compound of formula (I) starting from (III) and (II). Said deamination reaction is conveniently conducted by reaction with an acidic nitrite solution in the presence of an appropriate reductant, or by reaction with an alkylnitrite such as, for example, 1,1-dimethylethylnitrite or isoamylnitrite and the like. Preferably, said deamination reaction is conducted with an aqueous solution of nitrous acid or of a nitrite salt in a suitable acid in the presence of a reducing agent such as, for example, hypophosphorous acid, formic acid, at a lower temperature.

The compounds of formula (I) may also be prepared by reacting an intermediate of formula (V) with a reagent of formula (VI) such as, for example, a 1,1'-carbonyl-bis[1H-imidazole].

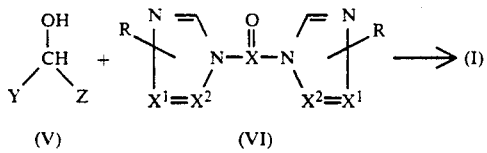

In (VI) X represents C or S.

Said reaction may conveniently be conducted in a suitable solvent such as, for example, an ether, e.g. 1,4-dioxane, tetrahydrofuran; a halogenated hydrocarbon, e.g. di- or trichloromethane; a hydrocarbon, e.g. benzene, methylbenzene, dimethylbenzene; N,N-dimethylformamide, N,N-dimethylacetamide, or a mixture of such solvents. In order to enhance the reaction rate, it may be advantageous to heat the reaction mixture.

The compounds of formula (I) may also be prepared by reacting a ketone] or aldehyde of formula (VII) with an azole (II) in the presence of formic acid or formamides as reducing agents.

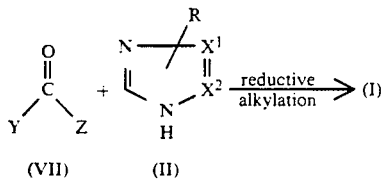

Said reductive alkylation can conveniently be conducted by stirring and heating the reagents in formic acid or formamides optionally in the presence of an acid catalyst. An appropriate acid catalyst for using in this reaction is for example a mineral acid such as, hydrochloric acid, sulfuric acid or a sulfonic acid such as, methanesulfonic acid, benzenesulfonic acid, 4-methylbenzenesulfonic acid and the like. It may be appropriate to remove the water which is formed during the reaction by azeotropical distillation, distillation, complexation and the like methods.

In all of the foregoing and following preparations, the reaction products may be isolated from the reaction mixture and, if necessary, further purified according to methodologies generally known in the art such as, for example, extraction, distillation, crystallization, trituration and chromatography.

Some compounds of formula (I) can alternatively be prepared under similar conditions as are described in the literature for the preparation of quinolines or quinolinones by cyclizing an intermediate of formula

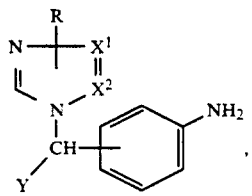

or an appropriate derivative thereof.

For example, the compounds of formula (I-a-1) can be prepared by cyclizing an intermediate of formula (IX).

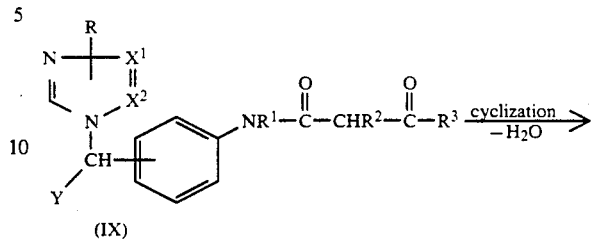

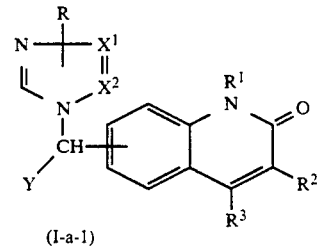

The acid-catalysed cyclization of (IX) can generally be conducted by treating the intermediate amide (IX) with an appropriate acid such as, for example, sulfuric acid, a hydrohalic acid, e.g. hydrochloric acid, polyphosphoric acid and the like storing acids, optionally at an enhanced temperature as described for example in J. Med. Chem. 1986, 29, 2427–2432.

The compounds of formula (I-a-1), may also be obtained by cyclizing an intermediate of formula (X).

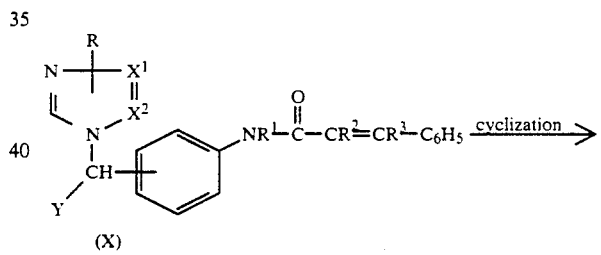

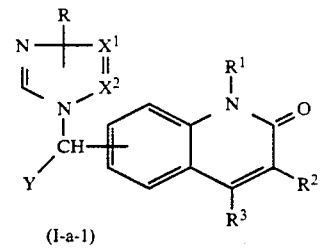

The cyclization reaction of (X) may be conducted according to art-known cyclizing procedures as described in, for example, Synthesis 1975, 739. Preferably the reaction is carried out in the presence of a suitable Lewis Acid, e.g. aluminum chloride either neat or in a suitable solvent such as, for example, an aromatic hydrocarbon, e.g. benzene, chlorobenzene, methylbenzene and the like; halogenated hydrocarbons, e.g. trichloromethane, tetrachloromethane and the like; an ether, e.g. tetrahydrofuran, 1,4-dioxane and the like or mixtures of such solvents. Somewhat elevated temperatures, preferably between 70°–100° C., and stirring may enhance the rate of the reaction.

Quinolinones of formula (I-a-1) may also be prepared by cyclizing an intermediate of formula (XI).

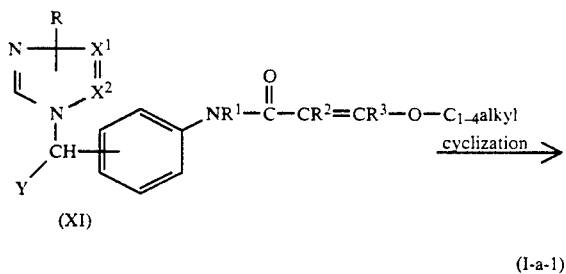

(XI)

(I-a-1)

The cyclization of (XI) can generally be conducted by treating the intermediate propeneamide (XI) with an appropriate acid such as, for example, sulfuric acid, a hydrohalic acid, e.g. hydrochloric acid, polyphosphoric acid and the like strong acids at room temperature or optionally at an enhanced temperature as described for examples in J. Med. Chem. 1989, 32,1552–1558 or J. Med. Chem. 1988, 31, 2048–2056.

Alternatively the compounds of formula (I) wherein Z is a radical of formula (a-1) or (a-2) may be prepared by cyclizing an intermediate of formula (XII) or (XIII).

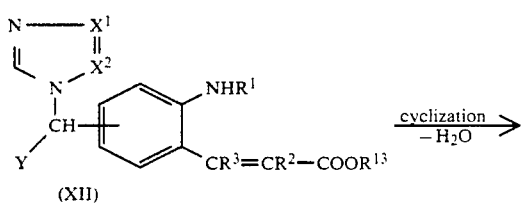

(XII)

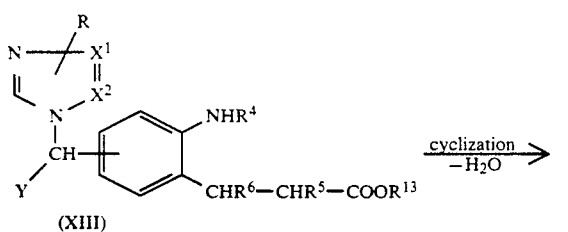

(I-a-1)

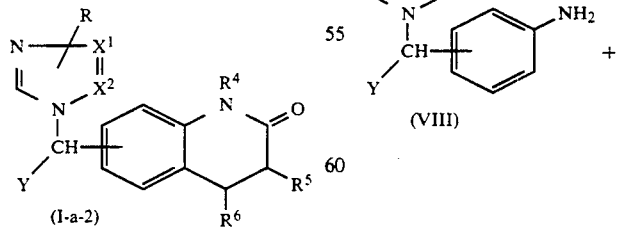

(XIII)

(I-a-2)

In (XII) and (XIII) $R^{13}$ represents either a hydrogen or a $C_{1-4}$alkyl group. The above mentioned cyclization reactions may be carried out by stirring and if desired heating the intermediate starting material, optionally in a suitable reaction-inert solvent. Appropriate solvents for said cyclization reactions are for example, aromatic hydrocarbons, e.g. benzene, methylbenzene, dimethylbenzene and the like; halogenated hydrocarbons, e.g. trichloromethane, tetrachloromethane, chlorobenzene and the like; ethers, e.g. 1,1'-oxybisethane, tetrahydrofuran, 1,4-dioxane, 1,2-dimethoxyethane and the like, alkanols, e.g. ethanol, propanol, butanol and the like; ketones, e.g. 2-propanone, 4-methyl-2-pentanone; dipolar aprotic solvents, e.g. N,N-dimethylformamide, dimethylsulfoxide, acetonitrile, methyl acetamide, pyridine and the like, or mixtures of such solvents. The water which is liberated during the cyclization reaction may be removed from the reaction mixture by azeotropical distillation.

Some compounds of formula (I-a-3), can be prepared by cyclizing an intermediate of formula (XIV).

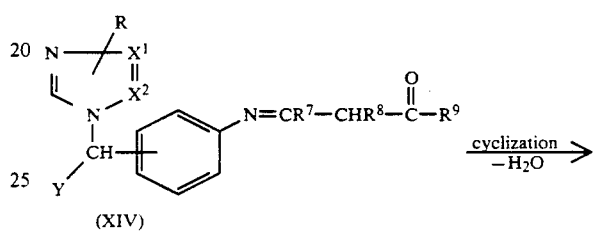

(XIV)

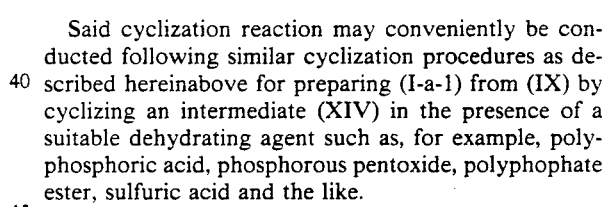

(I-a-3)

Said cyclization reaction may conveniently be conducted following similar cyclization procedures as deducted hereinabove for preparing (I-a-1) from (IX) by cyclizing an intermediate (XIV) in the presence of a suitable dehydrating agent such as, for example, polyphosphoric acid, phosphorous pentoxide, polyphophate ester, sulfuric acid and the like.

Alternatively the compounds of formula (I-a-3) can be prepared by reacting an aniline of formula (VIII) with an α,β-unsaturated carbonyl synthon of formula (XV) in the presence of an oxidizing agent.

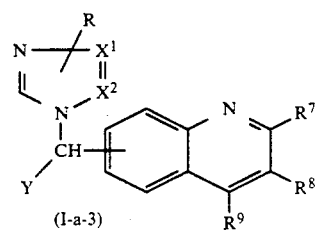

(VIII)

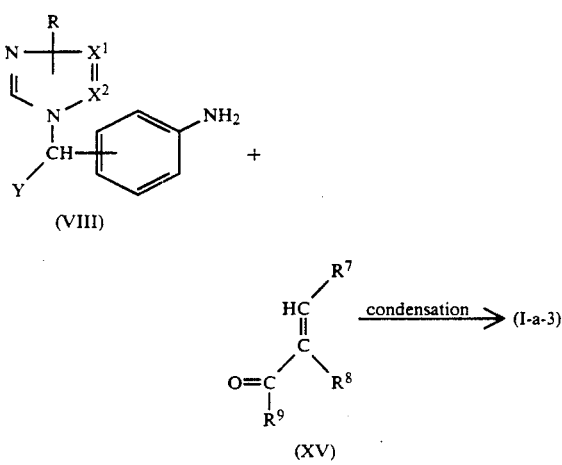

(XV)

Said reaction may be conducted by heating the reactants in the presence of an acid such as, for example, sulfuric acid, a hydrohalic acid, e.g. hydrochloric acid, polyphosphoric acid and the like strong acids and a mild oxidizing agent. Appropriate oxidizing agents are for example arsenic acid, arsenic oxide, boric acid, ferric chloride, silver nitrate, nitrobenzene, 4-nitrobenzenesulfonic acid or a mixture of 4-nitrobenzoic acid and 4-aminobenzoic acid and the like.

Compounds of formula (I-a-3) may also be prepared by condensing an ortho-acyl aniline of formula (XVI) with a ketone or aldehyde of formula (XVII).

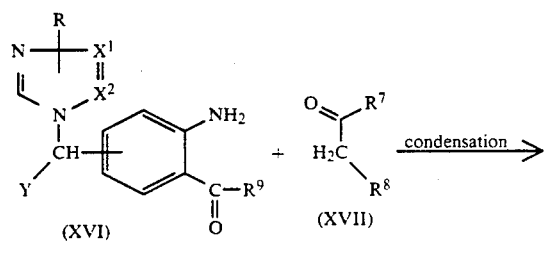

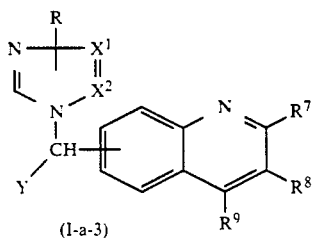

Said cyclization may conveniently be conducted by mixing the reactants in a reaction-inert solvent such as, for example, water, an alcohol, e.g. methanol, butanol and the like; an aromatic hydrocarbon, e.g. benzene, methylbenzene, dimethylbenzene and the like, an ester, e.g., ethyl acetate; a halogenated hydrocarbon, e.g., trichloromethane, dichloromethane and the like; or a mixture of such solvents, preferably in the presence of a mineral acid such as, for example, hydrochloric acid, sulfuric acid and the like, a carboxylic acid such as, for example, formic acid, acetic acid and the like, or a sulfonic acid such as, for example, methanesulfonic acid, benzenesulfonic acid, 4-methylbenzenesulfonic acid and the like or in the presence of a dehydrating agent, such as polyphosphoric acid, phosphorous pentoxide and the like. Somewhat elevated temperatures may be appropriate to enhance the rate of the reaction and in some cases the reaction may be carried out at the reflux temperature of the reaction mixture. It may be appropriate to remove the water which is liberated during the course of the condensation reaction by azeotropical distillation.

The compounds of formula (I) wherein Z is a radical of formula (a-4) and $R^{10}$ is hydrogen, said compounds being represented by (I-a-4-a) can be prepared by cyclizing an intermediate of formula (XVIII).

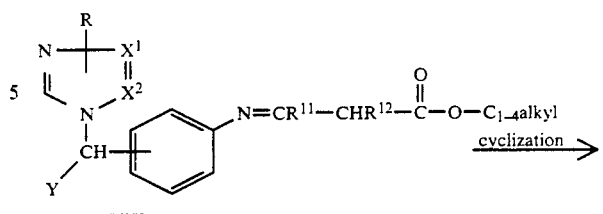

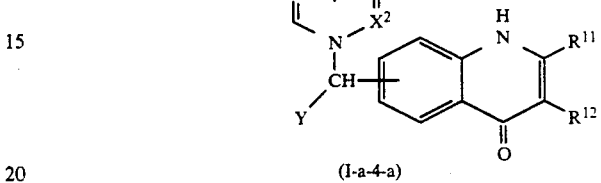

The above mentioned cyclization reaction is preferably accomplished by stirring the intermediate (XVIII) in the presence of a suitable dehydrating agent such as, for example, polyphosphoric acid, phosphorus pentoxide, polyphosphate ester, sulfuric acid and the like, if desired in a reaction inert solvent.

Alternatively, some compounds of formula (I) may also be prepared according to procedures analogous to those described in the literature of the preparation of azoles by cyclizing an appropriate starting material.

The compounds of formula (I-x) may also be prepared, for example, by cyclizing an intermediate of formula (XIX) and desulfurating the thus obtained intermediate of formula (XX).

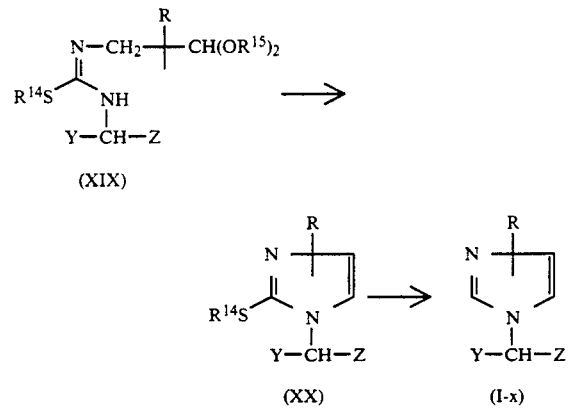

In formulae (XIX) and (XX) $R^{14}$ represents hydrogen or $C_{1-6}$alkyl and $R^{15}$ represents $C_{1-6}$alkyl or both $R^{15}$ taken together form a $C_{2-3}$alkanediyl radical.

Said cyclization reaction may conveniently be conducted by stirring and heating intermediate (XIX) in an aqueous acidic solvent, e.g. in aqueous hydrochloric or sulfuric acid. The intermediate (XX) may be desulfurated following art-known procedures, e.g., by treatment with Raney nickel in the presence of an alkanol, e.g. methanol, ethanol and the like, or by treatment with nitric acid, optionally in the presence of sodium nitrite.

The compounds of formula (I-y) may be prepared from a hydrazine derivative of formula (XXI) by reaction with s-triazine following the procedures described in J. Org. Chem., 1956, 1037.

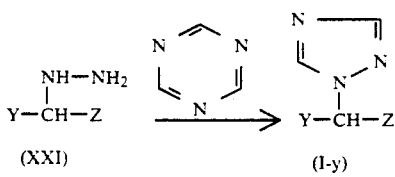

The intermediate hydrazine (XXI) and the corresponding intermediate amine of formula Y-CH(NH$_2$)-Z(XXII) may also advantageously be converted into azoles, wherein —X$^1$=X$^2$— is a bivalent radical of formula (x), (y) or (z), following the procedures described in U.S. Pat. NO. 4,267,179, incorporated herein by reference.

The compounds of formula (I) can also be converted into each other following art-known functional group transformation procedures.

The compounds of formula (I-a-1) wherein R$^1$ is hydrogen may be converted into compounds of formula (I-a-3) wherein R$^7$ is halo by treatment with a halogenating agent such as, for example, thionyl chloride, pentachlorophosphorane, phosphoryl chloride, sulfuryl chloride and the like. The thus obtained compounds of formula (I-a-3) wherein R$^7$ is halo may further be converted into compounds of formula (I-a-3) wherein R$^7$ is C$_{1-6}$-alkyloxy by reacting the starting compound with an appropriate alcohol, preferably an alkali metal or earth alkaline metal salt of said alcohol.

Depending on the nature of the substituents the compounds of formula (I-a-1) may also be converted into compounds of formula (I-a-2), by a selective hydrogenation of the starting compound with an appropriate reducing agent such as, for example with a nobel catalyst, such as platinum-on-charcoal, palladium-on-charcoal and the like. Dehydrogenation of the compounds of formula (I-a-2) may result in a compound of formula (I-a-1). The dehydrogenation may be accomplished by stirring and optionally heating the starting compound with alkaline peroxide, ammonical silver nitrate, 2,3-dichloro-5,6-dicyano-p-benzoquinone, manganese(IV-)oxide, bromine in the presence of bromobenzene and the like in suitable reaction-inert solvent. Suitable solvents for said dehydrogenation are, for example, water, alkanols, e.g. methanol, ethanol and the like, ketones, e.g. 2-propanone and the like, halogenated hydrocarbons, e.g. trichloromethane, tetrachloromethane and the like, ethers, e.g. 1,1-oxybisethane and the like, dipolar aprotic solvents, e.g. N,N-dimethylformamide, N,N-dimethylacetamide, pyridine and the like, or a mixture of such solvents. Some compounds of formula (I) may also be N-alkylated or N-aminated according to art known procedures.

A number of intermediates and starting materials in the foregoing preparations are known compounds which may be prepared according to art-known methodologies of preparing said or similar compounds. Some intermediates of the previous reaction schemes are novel and have especially been developed for conversion into compounds of the present invention.

Intermediates of formula (III), (V) and (VII-a) wherein Y is other than hydrogen may be prepared form an appropriately substituted quinoline or quinolinone derivative of formula (XXIII) according to the following reaction sequence.

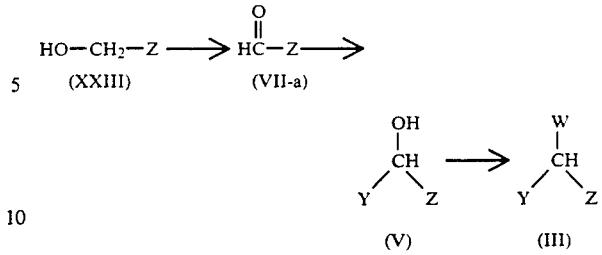

The hydroxymethyl moiety in the starting intermediate of formula (XXIII) is first converted into a formyl moiety with a suitable oxidant, e.g. manganese(IV) oxide or potassium permanganate, and subsequently reacted with a metal alkyl, e.g. methyl-lithium, butyllithium, metal aryl, e.g. phenyllithium, or with a complex metal alkyl or aryl in a suitable solvent, e.g. tetrahydrofuran, 1,1'-oxybisethane and the like to form the secondary alcohols (V). The desired intermediates of formula (III) may then be obtained by converting the alcohol function of the intermediate of formula (V) into an appropriate leaving group W following standard procedures as known in the art. For example, halides are generally prepared by the reaction of (V) with an appropriate halogenating agent such as, for example, thionyl chloride, sulfuryl chloride, pentachlorophosphorane, pentabromophosphorane, phosphorylchloride, hydrochloric acid, hydrobromic acid and the like halogenating agents. The intermediates of formula (III) wherein Y is hydrogen can be obtained directly from the intermediates of formula (XXIII) following the procedure described hereinabove for converting (V) into (III).

Some intermediates of formula (III) wherein Y is other than hydrogen may also be prepared by acylating a quinoline or quinolinone of formula (XXV) with an appropriate reagent of formula (XXIV) according to art-known Friedel-Crafts acylation reaction procedures, reducing the thus obtained ketone (VII-b) with an appropriate reductant, e.g. sodium borohydride in a suitable solvent such as water; an alcohol e.g. methanol, ethanol or mixtures thereof with tetrahydrofuran optionally in the presence of sodium hydroxide and subsequently converting the alcohol function into an appropriate leaving group as described hereinbefore.

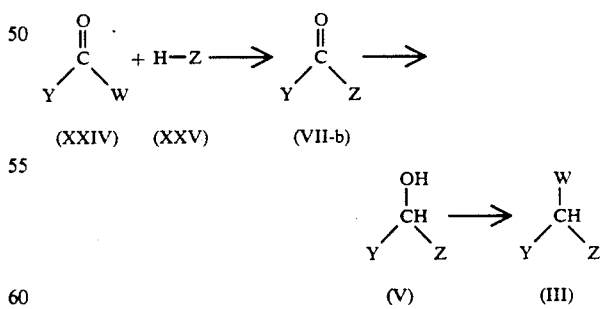

Some intermediates of formula (III) may also be prepared by cyclizing an appropriate benzaldehyde or ketone derivative of the general formula (XXVI) according to similar cyclization procedures as described hereinabove for the synthesis of the compounds of formula (I-a-1),(I-a-2),(I-a-3) or (I-a-4), reducing the thus obtained quinoline or quinolinone with an appropriate reductant, e.g. sodium borohydride, sodium cyanoborohydride and the like reagents and subsequently converting the alcohol function of (V) in an appropriate leaving group. Depending on the cyclization procedure it may be useful to protect the ketone or aldehyde group according to art known procedures e.g. by acetalization.

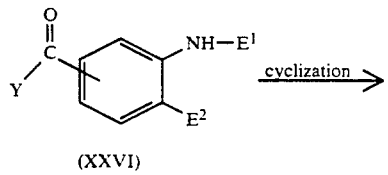

(XXVI)

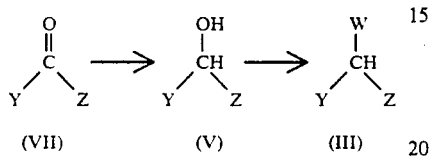

(VII) (V) (III)

In (XXVI) the meanings of $E^1$ and $E^2$ are selected in such a manner to enable a cyclization reaction. For example, as appropriate intermediates of formula (XXVI) there may be mentioned:

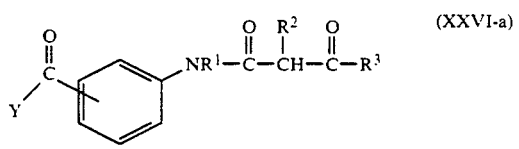

(XXVI-a)

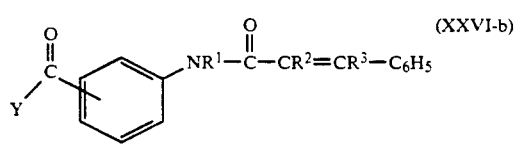

(XXVI-b)

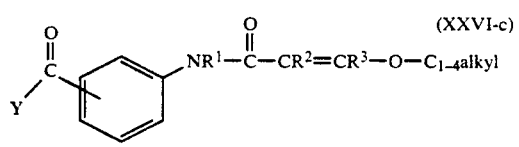

(XXVI-c)

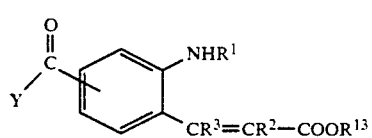

(XXVI-d)

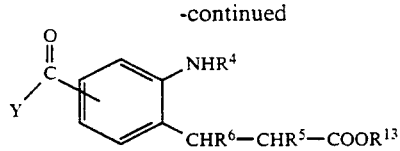

(XXVI-e)

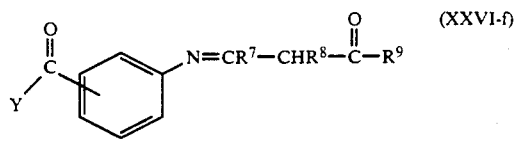

(XXVI-f)

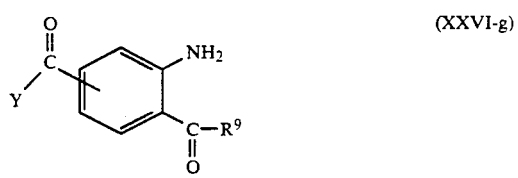

(XXVI-g)

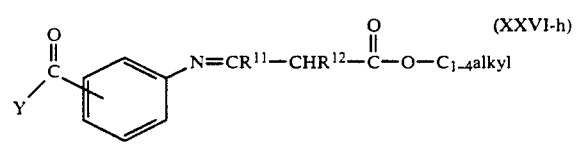

(XXVI-h)

Intermediates of formula (IX),(X) and (XI) can conveniently be prepared by reacting an aniline (VIII-a) with respectively a carboxylic acid of formula (XXVII-a), (XXVII-b) or (XXVII-c) or a functional derivative thereof.

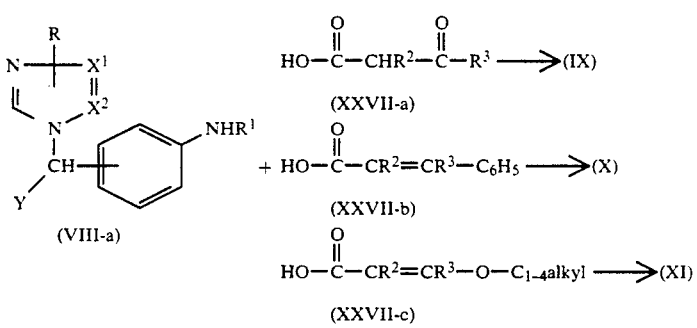

(VIII-a) (XXVII-a)

(XXVII-b)

(XXVII-c)

Said functional derivatives of formula (XXVII-a), (XXVII-b) and (XXVII-c) are meant to comprise the halide, anhydride, amide and ester forms of (XXVII-a), (XXVII-b) and (XXVII-c). (XXVII-a) may also be in the form of a reactive lactone such as, for example, 4-methylene-2-oxetanone.

Functional derivatives may be prepared following art-known procedures, for example, by reacting the carboxylic acid of formula (XXVII) with thionyl chloride, phosphorous trichloride, polyphosphoric acid, phosphoryl chloride and the like, or by reacting the carboxylic acid of formula (XXVII) with an acyl halide, e.g. acetyl chloride, ethyl carbonochloridate and the like. Or the intermediates (VIII-a) and (XXVII) may be coupled in the presence of a suitable reagent capable of forming amides, e.g. 1,1'-carbonylbis[1H-imidazole], dicyclohexylcarbodiimide, 2-chloro-1-methylpyridinium iodide and the like.

Said amidation reactions may conveniently be carried out by stirring the reactants in a suitable reaction-inert solvent, such as, for example, a halogenated hydrocarbon, e.g. dichloromethane, trichloromethane and the like, an aromatic hydrocarbon, e.g. methylbenzene and the like, an ether, e.g. 1,1'-oxybisethane, tetrahydrofuran and the like or a dipolar aprotic solvent, e.g. N,N-dimethylformamide, N,N-dimethylacetamide and the like. The addition of a suitable base may be appropriate, in particular a tertiary amine such as, N,N-diethylethanamine. The water, the alcohol or the acid which is liberated during the course of the reaction may be removed from the reaction mixture according methodologies generally known in the art such as, for example, azeotropical distillation, complexation and salt formation.

When a reactive lactone of formula (XXVII-a) is used the reaction may be carried out according to similar procedures as outlined in Organic Synthesis, Willy New York, 1955, Collect. Vol. III page 10.

The intermediate of formula (XII) and/or (XIII) can be prepared by reducing the nitro derivative of formula (XXVIII) in the presence of hydrogen and a suitable metal catalyst such as, for example, palladium-on-charcoal, platinum oxide and the like catalysts. The nitro derivative of formula (XXVIII) in turn can be prepared from an aldehyde of formula (XXIX) by reacting the latter with a phosphorous ylide of formula (XXX) or with an ylide of formula (XXXI) prepared from a phosphonate.

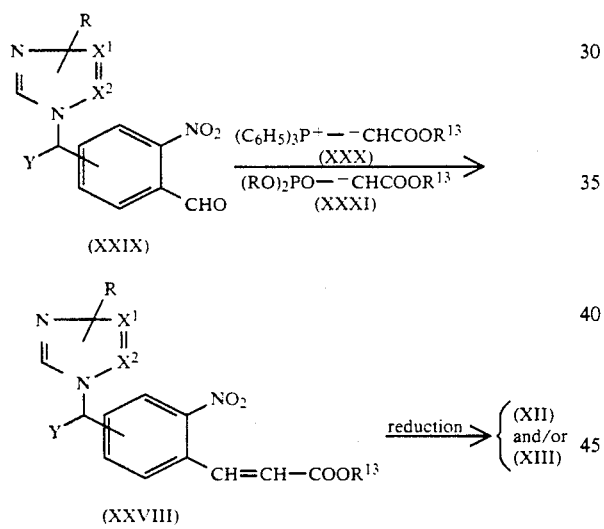

In formula (XXVIII) $R^{13}$ represents hydrogen or $C_{1-4}$alkyl.

The reaction of (XXIX) with (XXX) or (XXXI) can conveniently be conducted by treating a phosphonium salt or a phosphonate with an appropriate base such as, for example, butyllithium, methyllithium, sodium amide, sodium hydried, a sodium or potassium alkoxide, sulfinylbis(methane) sodium salt and the like bases, under an inert atmosphere and in a reaction-inert solvent such as for example, a hydrocarbon, e.g. hexane, heptane, cyclohexane and the like; an ether, e.g. 1,1'-oxybisethane, tetrahydrofuran, 1,2-dimethoxyethane and the like; a dipolar aprotic solvent, e.g. dimethylsulfoxide, hexamethylphosphor triamide, and the like solvents.

The starting intermediate (XXIX) wherein the 1H-azole-1-ylmethyl moiety is substituted in the para position can for example be prepared according the following reaction sequence.

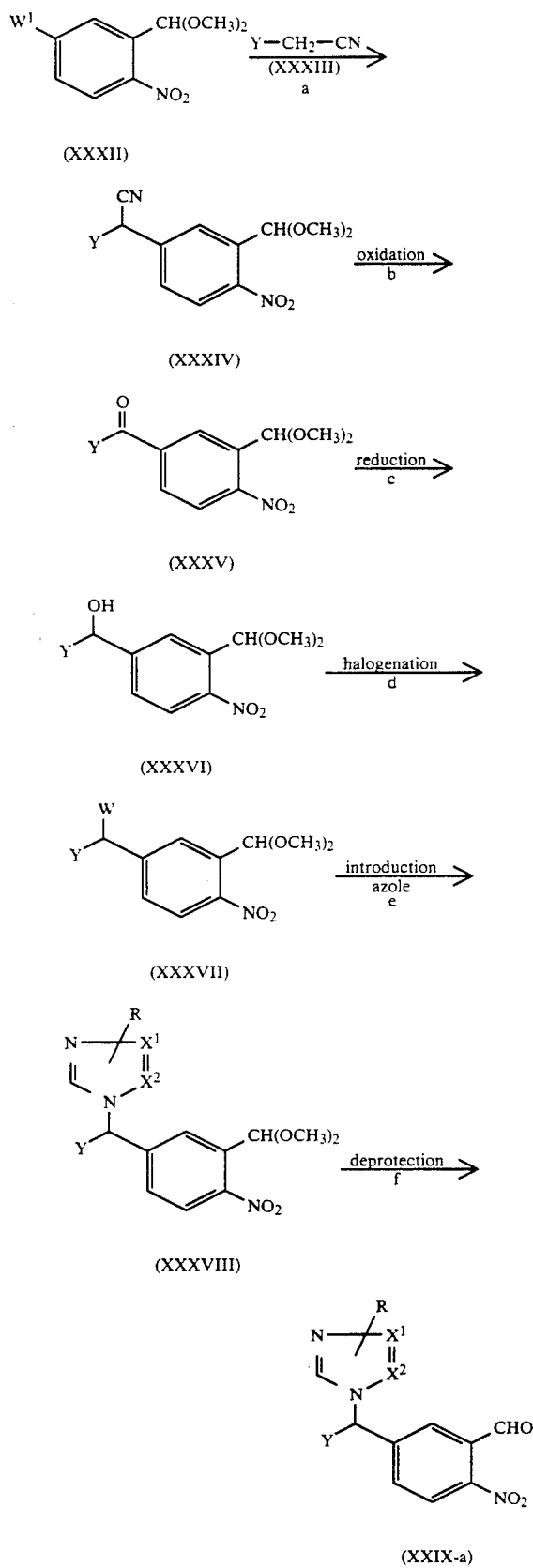

In formula (XXXII) $W^1$ represents a reactive leaving group such as, for example, halo, e.g. chloro or fluoro, nitro, 4-methylbenzenesulfonyloxy, phenyloxy, alkyloxy and the like groups.

a) The aromatic nucleophilic substitution on a nitrobenzene of formula (XXXII) with a cyanide of formula (XXXIII) can be conducted by stirring the reactants in the presence of a base in a reaction inert solvent such as for example, a dipolar aprotic solvent, e.g. N,N-dimethylformamide, N,N-dimethylacetamide, hexamethylphosphoric triamide, pyridine, 1,3-dimethyl-3,4,5,6-tetrahydro-2(1H)-pyrimidinone, 1,3-dimethylimidazolidinone, 1,1,3,3-tetramethylurea, 1-methyl-2-pyrrolidinone, nitrobenzene and the like solvents; or mixtures thereof. Appropriate bases are sodium hydride, sodium amide, sulfinylbis(methane) sodium salt and the like bases. It may be advantageous to add to the reaction mixture a crown ether, e.g. 1,4,7,10,13,16-hexaoxacyclooctadecane and the like or a complexing agent such as for example, tris[2-(2-methoxyethoxy)]ethanamine and the like. Somewhat elevated temperatures may enhance the rate of the reaction.

b) The oxidation of the cyanide of formula (XXXIV) can be accomplished following art-known oxidation procedures as described in J. Org. Chem., 1975, 40, 267.

c) The reduction of the aldehyde or ketone of formula (XXXV) can be carried out by stirring the latter with an appropriate reductant, e.g. sodium borohydride in a suitable solvent, e.g. methanol, ethanol.

d) The halogenation of the alcohol of formula (XXXVI) can be accomplished by reacting the alcohol with a suitable halogenating agent, e.g., thionyl chloride, methanesulfonyl chloride and the like.

e) The introduction of the azole can be carried out according procedures outlined hereinbefore for the synthesis of (I) from (II) and (III).

f) The deprotection of the carboxaldehyde group of (XXXVIII) can easily be conducted following art-known methods of hydrolyzing acetals, e.g. by acid hydrolysis in an aqueous medium.

The intermediates of formula (XIV) and (XVIII) may be prepared by reacting an aniline of formula (VIII) with a 1,3-dicarbonyl of formula $R^7$—C(=O)—CH-$R^8$—C(=O)—$R^9$ (IXL) or $R^{11}$—C(=O)—CHR$^{12}$—C(-=O)—O—$C_{1-4}$alkyl (XL) in a reaction-inert solvent in the presence of an appropriate acid catalyst such as, for example, a sulfonic acid, e.g. methanesulfonic acid, benzenesulfonic acid, 4-methylbenzene sulfonic acid and the like acids.

The starting compounds of formula (VIII) can easily be prepared according to procedures described in U.S. Pat. No. 4,859,684 corresponding to EP-A-260,744 incorporated herein by reference for the process of preparing the intermediate of formula (VIII).

The intermediate hydrazines (XXI) and amines (XXII) may conveniently be prepared from a ketone of formula (VII) by reaction with either an acid addition salt thereof, or with hydroxylamine or hydrazine or an acid addition salt or a solvate thereof, and reducing the thus obtained oxime or hydrazone, for example, by catalytic hydrogenation in the presence of hydrogen and an appropriate hydrogenation catalyst, e.g. Raney nickel and the like.

The intermediate of formula (XIX) can be prepared from an amine of formula (XXII) by reaction with a reagent of formula (XLI) and optionally X-alkylating the thus obtained thiourea with a $C_{1-6}$alkylhalide.

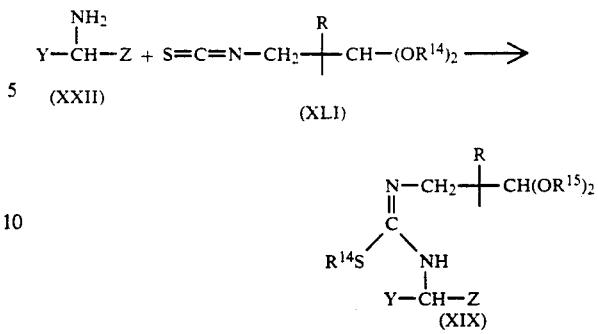

The compounds of formula (I) and some of the intermediates in this invention have an asymmetric carbon atom in their structure. This chiral center may be present in a R- and a S-configuration, this R- and S-notation being in correspondence with the rules described in Pure Appl. Chem., 1976, 45, 11-30. Pure stereochemically isomeric forms of the compounds of this invention may be obtained by the application of art-known procedures. Diastereoisomers may be separated by physical separation methods such as selective crystallization and chromatographic techniques, e.g. counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

The compounds of the present invention, their pharmaceutically acceptable acid addition salts and their possible stereochemically isomeric forms have useful pharmacoldogical properties. For example, they suppress the plasma elimination of retinoids, such as, all-trans-retinoic acid, 13-cis retinoic acid and their derivatives. The latter results in more sustained/higher tissue concentrations of retinoic acid and improved control of the differentiation and growth of various cell types. In addition some compounds inhibit the formation of androgens from progestines and/or inhibit the action of the enzyme complex aromatase which catalyses the formation of estrogens from androgenic steroids in mammals. A number of compounds also show an inhibitory action on the biosynthesis of thromboxane $A_2$.

Said property of the compounds of the invention to delay the metabolism of retinoic acid can easily be evidenced in various in vivo experiments. A particular test procedure is described hereinafter as the "Metabolism of endogenous or exogenously administered all-trans-retinoic acid" test and demonstrates the suppression of he plasma elimination of endogenous or exogenously administered all-trans-retinoic acid. As such, the compounds of formula (I) can be used to control the rate of growth and differentiation of various cell types which effects are known to be affected by retinoids. The ability of retinoids, such as, 13-cis-retinoic acid, all-trans-retinoic acid and their derivatives to modulate differentiation and proliferation in several cell types whether they are of epithelial or mesenchymal origin is extensively studied and reviewed in J. Clin. Chem. Clin, Biochem., 26, 479-488 (1983); Pharmacological Reviews 36, 935-1005, (1984), Arch. Dermatol. 117, 160-180; (1981) and Journal of Medicinal Chemistry 25, 1269-1277, (1982).

In view of their capability to delay the metabolism of retinoic acid the compounds can thus be used in the treatment of disorders which are characterized by an increased proliferation and/or abnormal differentiation of epithelial cells. In particular the compounds of the invention can be used for treatment of carcinoma which is essentially a derailment of cellular differentiation, occurring in epithelial tissues. Other uses include, in addition to cancer treatment, the treatment of a variety of disorders of keratinization such as, for example, acne, psoriasis, lamellar ichthyosis, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis plamaris et plantaris, and similar diseases.

The anti-tumor activity may be demonstrated in several retinoic acid-sensitive and insensitive cell lines and solid tumors such as, for example, in Ta3-Ha induced mamma tumors in female mice.

The inhibition of androgen and/or estrogen formation can be demonstrated by analyzing the effects of the compounds of the invention on the conversion of progestins into androgens in the presence of testicular microsomes or on the conversion of androstenedione into estrone and estradiol in the presence of human pacental microsomes. The in vivo-inhibition of androgen or estrogen formation can, for example, be demonstrated by measuring the suppression of the plasma testosterone or estrogen concentration in dogs, rats or mice. A number of relevant tests have been described in EP-A-260,744 and EP-A-293,978, both incorporated herein by reference. In view of their capability to inhibit the biosynthesis of estrogens and/or androgens the compounds can be used in the treatment of estrogen or androgen or androgen dependent disorders such as, for example, breast cancer, endometriosis, endometrial cancer, polycystic ovarian disease, benign breast, endometriosis, endometrial cancer, polycystic ovarian disease, benign breast disease, prostatic cancer and hirsutism.

The beneficial effect of androgen inhibitors in these disorders, especially in the treatment of prostatic cancer, is described in e.g., Journal of Urology 132, 61–63 (1984). The beneficial effect of aromatase inhibitors in these disorders, especially in the treatment of breast cancer, is described in, e.g. Cancer Research, 42, Suppl. 8:3261s (1982).

In view of the usefulness of the subject compounds it is evident that the present invention provides a method for treating mammals suffering from disorders which are characterized by an increased proliferation and/or abnormal differentiation of normal, preneoplastic or neoplastic cells, whether they are epithelial or mesenchymal; whether they are of ectodermal or mesodermal origin; or whether they are estrogen dependent, androgen dependent or nonestrogen and nonandrogen dependent. Said method comprises the systemic or topical administration to the latter of an amount, effective to treat said disorders, of a compound of formula (I), a pharmaceutically acceptable acid-addition salt, or a possible stereochemically isomeric form thereof. In particular the present invention provides a method in which the growth and differentiation in said normal, preneoplastic and neoplastic cells is sensitive to the actions of reinoids.

Those of skill in treating disorders which are characterized by an excessive proliferation and/or abnormal differentiation of tissues could determine the effective amount from the test results presented hereinafter. In general it is contemplated than an effective amount would be from 0.0001 mg/kg to 50 mg/kg body weight and more preferably from 0.01 mg/kg to 10 mg/kg body weight.

The subject compounds may be formulated into various pharmaceutical forms for administration purposes. As appropriate compositions there may be cited all compositions usually employed for systemically or topically administering drugs. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, precutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprise saline solution, glucose solution or a mixture of saline and glucose solution. Injectable suspensions may also be prepared in which case appropriate liquid carriers, suspending agents and the like may be employed. Also included are solid from preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

As appropriate compositions for topical application there may be cited all compositions usually employed for topically administering drugs, e.g., creams, gellies, dressings, shampoos, tinctures, pastes, ointments, salves, powders and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

Other such compositions are preparations of the cosmetic type, such as toilet waters, packs, lotions, skin milks or milky lotions. Said preparations contain, besides the active ingredient, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other agents.

Examples of oils comprise fats and oils such as olive oil and hydrogenated oils; waxes such as beeswax and lanolin; hydrocarbons such as liquid paraffin, ceresin, and squalane, fatty acids such as stearic acid and oleic acid, alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene lauryl-ether phosphate, sodium N-acyl glutamate; cationic surfactants such as stearyldimethyl-benzylammonium chloride and stearyltrimethylammonium chloride; ampholytic surfac-tants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monosterate, polyoxyethylene sorbitan monopalmitate, polyoxyethylene coconut fatty acid monoethanolamide, polyoxyethylene polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy disphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid. For preparing ointments, creams, toilet waters, skin milks, and the like, typically from 0.01 to 10% in particular from 0.1 to 5% and more in particular from 0.2 to 2.5% of the active ingredient will be incorporated in said compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener, or 5 to 15% of a surfactant, 2-15% of a humectant, 0 to 80% of an oil, very small (<2%) amounts of preservative, colouring agent and/or perfume, and water. In a toilet water, the carrier for example consists of 2 to 10% of a lower alcohol, 0.1% to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the afore-mentioned preparations, all % symbols refer to weight by weight percentage. The humectant, surfactant, oil, etc., referred to in said preparations may be any such component used in the cosmetic arts but preferably will be one or more of the components mentioned hereinabove. Further, when in the above compositions one or more of the components make up the major part of the composition, the other ingredients can evidently be not present at their indicated maximum concentration and therefore will make up the remainder of the composition.

Particular compositions for use in the method of the present invention are those wherein the active ingredient is formulated in liposome-containing compositions. Liposomes are artificial vesicles formed by amphiphatic molecules such as polar lipids, for example, phosphatidyl cholines, ethanolamines and serines, sphingomyelins, cardiolipins. plasmalogens, phosphatidic acids and cerebiosides. Liposomes are formed when suitable amphiphatic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

In a further aspect of the invention there are provided particular pharmaceutical or cosmetical compositions which comprise an inert carrier, an effective amount of a compound of formula (I) an acid addition salt or a stereochemically isomeric form thereof and an effective amount of a retinoic acid, a derivative thereof or a stereochemically isomeric form thereof. Said retinoic acid containing compositions are particularly useful for treating acne or for retarding the effects of aging of the skin and generally improve the quality of the skin, particularly human facial skin. A pharmaceutical or cosmetical composition containing retinoic acid or a derivative thereof as the active ingredient in intimate admixture with a dermatologically acceptable carrier can be prepared according to conventional compounding techniques, such as those known for topical application of retinoic acid and its derivatives. Conventional pharmaceutical compounding techniques for topical application of retinoic acid are described for example in, U.S. Pat. Nos. 3,906,108 and 4,247,547, which are incorporated herein by reference. Preferred composition for topical application are in form of a cream, ointment or lotion comprising from 0.005 to 0.5% (particularly from 0.01 to 0.1%) all-trans-retinoic acid, 13-cis-retinoic acid or a derivative thereof and from 0.1 to 5% of a compound of formula (I) and, a dermatologically acceptable acid addition salt thereof or a stereochemically isomeric form thereof, in a semi-solid or liquid diluent or carrier. These preferred compositions should preferably be non-irritating and as far as possible they should be odorless and non-toxic. For convenience in applying to the skin, the composition usually contain, besides water or an organic solvent, several of certain organic emollients, emulsifiers for the aqueous and/or non aqueous phases of the compositions, wetting agents preservatives and agents that facilitate the penetration and remainence of the active agents in the skin.

The following examples are intended to illustrate and not to limit the scope of the present invention. Unless otherwise stated all parts therein are by weight.

EXPERIMENTAL PART

A. Preparation of the intermediates

Example 1 a) A mixture of 8.6 parts of 7-quinolinemethanol, 20 parts of manganese(IV)oxide and 130 parts of dichloromethane was stirred for 24 hours at room temperature. The reaction mixture was filtered over diatomaceous earth and the filtrate was evaporated. The residue was purified by column chromatography (silica gel; $CH_2Cl_2/CH_3OH$ 98:2). The eluent of the desired fraction was evaporated, yielding 8 parts (94.2%) of 7-quinolinecarboxaldehyde; mp. 56° C.(interm. 1).

b) To a stirred mixture of 1.25 parts of magnesium, 14 parts of 1,1'-oxybisethane and 8 parts of bromobenzene was added a solution of 8 parts of intermediate 1, namely 7-quinolinecarboxaldehyde, in 72 parts of tetrahydrofuran, keeping the temperature between 0° C. and 5° C. After stirring for 12 hours at room temperature, the reaction mixture was poured into 300 parts of ice-water. The product was extracted with 1,1'-oxybisethane (3×70 parts). The combined extracts were dried, filtered and evaporated. The residue was purified by column chromatography (silica gel; $CH_2Cl_2/CH_3OH$ 98:2). The eluent of the desired fraction was evaporated, yielding 3.2 parts (26.6%) of α-phenyl-7-quinolinemethanol; mp. 118° C.(interm. 2).

In a similar manner there were also prepared the intermediates listed in Table 1.

TABLE 1

OH
|
R—CH—[quinoline]

| Int. No. | R | physical data (mp. in °C.) |
|---|---|---|
| 3 | $C_6H_5$ | 98 |
| 4 | 3-$ClC_6H_4$ | 112 |
| 5 | 3-$FC_6H_4$ | 94 |
| 6 | 4-$ClC_6H_4$ | 148 |
| 7 | 3-$CH_3C_6H_4$ | 122 |
| 8 | 3-$CH_3OC_6H_4$ | 142 |
| 9 | 3,4-di(F)$C_6H_3$ | — |
| 10 | 3,4-di($CH_3$)$C_6H_3$ | 114 |
| 11 | 3-$CF_3C_6H_4$ | — |
| 12 | 4-$FC_6H_4$ | 128 |
| 13 | 4-$CH_3OC_6H_4$ | 164 |
| 14 | 4-$CH_3C_6H_4$ | 135 |
| 15 | c-$C_6H_{11}$ | 118 |

Example 2 a) A mixture of 34 parts of 6-quinolinemethanol, 70 parts of manganese(IV)oxide and 300 parts of trichloromethane was stirred for 24 hours at room temperature. The reaction mixture was filtered over diatomaceous earth and the filtrate was evaporated, yielding 27.7 parts (82.7%) of 6-quinolinecarboxaldehyde; mp. 72° C. (interm. 16).

b) To a stirred and cooled (−5/0° C.) solution of 5.4 parts of thiophene in 21.3 parts of 1,1'-oxybisethane were added portionwise 43.5 parts of a solution of n. butyllithium in hexanes 1.6M. After stirring for 20 min. at 0° C., there was added a solution of 5 parts of intermediate 16, namely 6-quinolinecarboxaldehyde, in 71.2 parts of tetrahydrofuran. Stirring at 0° C. was continued for 1 hour and then the reaction mixture was poured into 200 parts of ice-water. The product was extracted with 1,1'-oxybisethane and the extract was dried, filtered and evaporated. The residue was purified by column chromatography (silica gel; $CH_2Cl_2/CH_3OH$ 95:5). The eluent of the desired fraction was evaporated, yielding 2.4 parts (31.1%) of α-(2-thienyl)-6-quinolinemethanol (interm. 17).

Example 3 a) To a stirred amount of 45.3 parts of aluminiumtrichloride were added dropwise 6.9 parts of N,N-dimethylformamide. After stirring for 5 min. at 70° C., there were added portionwise 5 parts of 3,4-dihydroquinolin-2(1H)-one and, after another 5 min., 4.7 parts of benzoylchloride. Stirring at 70° C. was continued for 2 hours and then the reaction mixture was carefully poured into ice-water. There were added 50 ml of HCl 12N and the whole was stirred for 15 min. The precipitate was filtered off and boiled in 2-propanol. The product was filtered off, washed with 2-propanol and 2,2'-oxybispropane and dried in vacuo at 60° C., yielding 6.3 parts (73.8%) of 6-benzoyl-3,4-dihydro-2(1H)-quinolinone; mp. 211.0° C. (interm. 18).

b) To a suspension of 27.3 parts of intermediate 18, namely 6-benzoyl-3,4-dihydro-2(1H)-quinolinone, in 790 parts of methanol were added 115 parts of an aqueous sodium hydroxide solution 1N. After stirring for 10 min., there were added at once 4.54 parts of sodium tetrahydroborate. Stirring was continued over weekend at room temperature. There were added 110 ml of HCl 1N and 1000 parts of water. The precipitate was filtered off, stirred in water for 15 min and then taken up in a mixture of methanol and methylbenzene. This solution was evaporated and the residue was coevaporated with methylbenzene. The product was filtered off and dried at 70° C., yielding 21.9 parts (78.6%) of 3,4-dihydro-6-(hydroxyphenylmethyl)-2(1H)-quinolinone; mp. 175.0° C. (interm. 19). In a similar manner there were also prepared:

6-[(3-chlorophenyl)hydroxymethyl]-3,4-dihydro-2(1H)-quinolinone; mp. 181.1° C. (interm. 20);

3,4-dihydro-6-(1-hydroxyethyl)-2(1H)-quinolinone; mp. 174.5° C. (interm. 21); and 3,4-dihydro-6-[hydroxy(isopropyl)methyl]-2(1H)-quinolinone; mp. 194.4° C. (interm. 22).

Example 4

A mixture of 3.2 parts of intermediate 2, namely α-phenyl-7-quinolinemethanol, 8 parts of thionyl chloride and 65 parts of dichloromethane was stirred for 4 hours at room temperature. The reaction mixture was evaporated and the residue was poured into water. The product was extracted with dichloromethane (3×39 parts) and the combined extracts were dried, filtered and evaporated, yielding 3.4 parts (98.5%) of 7-(chlorophenylmethyl)quinoline (interm. 23). In a similar manner there were also prepared the intermediates listed in Table 2.

TABLE 2

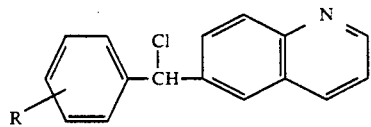

| Int. No. | R |
|---|---|
| 24 | 3-Cl |
| 25 | H |
| 26 | 3-F |
| 27 | 4-Cl |
| 28 | 3-CH$_3$ |
| 29 | 3-CH$_3$O |
| 30 | 3,4-di(F) |
| 31 | 3,4-di(CH$_3$ |
| 32 | 3-CF$_3$ |
| 33 | 4-CH$_3$ |
| 34 | 4-F |
| 35 | 4-CH$_3$O |

Example 5

To a stirred mixture of 2 parts of intermediate 21, namely 3,4-dihydro-6-(1-hydroxyethyl)-2(1H)-quinolinone in 8.9parts of tetrahydrofuran were added 1.62 parts of thionyl chloride. Stirring at room temperature was continued overnight. The reaction mixture was evaporated and the residue was co-evaporated with methylbenzene, yielding 2.3 parts (93.4%) of 6-(1-chloroethyl)-3,4-dihydro-2(1H)-quinolinone hydrochloride (interm. 36).

Example 6

A mixture of 20 parts of intermediate 19, namely 3,4-dihydro-6-(hydroxyphenylmethyl)-2(1,H)-quinolinone and 355 parts of a solution of hydrobromic acid in acetic acid 30% was stirred overnight at room temperature. The reaction mixture was evaporated and the residue was stirred in ethyl acetate. The product was filtered off, washed with ethyl acetate and 2,2'-oxybispropane and dried in vacuo at 35° C., yielding 23 parts (67.2%) of 6-[bromophenylmethyl]-3,4-dihydro-2(1H)-quinolinone hydrobromide dihydrate; mp. 119.5° C. (interm. 37). In a similar manner there were also prepared:
6-[bromo(3-chlorophenyl)methyl]3,4-dihydro-2(1H)-quinolinone hydrobromide (interm. 38); and
6-[bromocyclohexylmethyl]quinoline (interm. 39).

Example 7 a) To a stirred and cooled (0° C.) amount of 55.2 parts of sulfuric acid were added portionwise 13 parts of 1-(2-methyl-1-phenylpropyl)-1H-imidazole mononitrate. After stirring for ½ hour at 0° C., the reaction mixture was poured into ice-water. The whole was basified with ammonia and extracted with dichloromethane. The extract was dried, filtered and evaporated, yielding 12 parts (97.8%) of 1-[2-methyl-1-(4-nitrophenyl)propyl]-1H-imidazole (interm. 40).

b) A mixture of 12 parts of intermediate 40, namely 1-[2-methyl-1-(4-nitrophenyl)propyl]-1H-imidazole, and 79 parts of methanol was hydrogenated for 1 hour at room temperature and 2.10$^5$ Pa with 3 parts of Raney nickel. The catalyst was filtered off and the filtrate was evaporated, yielding 12 parts (100%) of 4-[1-(1H-imidazol-1-yl)-2-methylpropyl]benzenamine (interm. 41).

Example 8 a) To a stirred solution of 88.7 parts of 1-[chlorophenylmethyl]-4-nitrobenzene in 790 parts of acetonitrile were added 121.8 parts of 1Himidazole. After stirring for 24 hours at reflux temperature, the reaction mixture was evaporated. The residue was taken up in methylbenzene. This solution was washed with K$_2$CO$_3$ (aq.), dried, filtered and evaporated. The residue was purified by column chromatography (silica gel; CH$_2$Cl$_2$/CH$_3$OH 98:2). The eluent of the desired fraction was evaporated, yielding 53 parts (53%) of 1-[(4-nitrophenyl)phenylmethyl]-1H-imidazole (interm. 42).

b) A solution of 39 parts of intermediate 42, namely 1-[(4-nitrophenyl)phenylmethyl]-1H-imidazole, in 240 parts of ethanol was hydrogenated at 3.10$^5$ Pa and at room temperature with 20 parts of Raney nickel. After the calculated amount of hydrogen was taken up, the catalyst was filtered off and the filtrate was evaporated, yielding 34.6 parts (99.1%) of 4-[(1H-imidazol-1-yl)phenylmethyl]-benzenamine (interm. 43). In a similar manner there were also prepared:
4-[(4-fluorophenyl)(1H-imidazol-1-yl)methyl]benzenamine (interm. 44); and
4-[(4-chlorophenyl)(1H-imidazol-1-yl)methyl]benzenamine (interm. 45).

Example 9 a) To a stirred and cooled (0° C.) mixture of 5 parts of N-[4-[(3-chlorophenyl)hydroxymethyl]phenyl]acetamide, 66.5 parts of dichloromethane and 5.5 parts of N,N-diethylethanamine was added a solution of 3.1 parts of methanesulfonyl chloride in 13.3 parts of dichloromethane under a nitrogen atmosphere. After stirring for 1 hour, the reaction mixture was evaporated, yielding 8 parts (100%) of 4-(acetylamino)-α-(3-chlorophenyl)benzenemethanol methanesulfonate(ester)(interm. 46).

b) A mixture of 8 parts of intermediate 46, namely 4-(acetylamino)-α-(3-chlorophenyl) benzenemethanol methanesulfonate(ester), 10 parts of 1H-imidazole and 39.5 parts of acetonitrile was stirred for 2 hours at reflux temperature. The reaction mixture was evaporated and the residue was extracted with ethyl acetate. The extract was washed with NaHCO$_3$ (aq.), dried, filtered and evaporated, yielding 18 parts (100%) of N[4-[(3-chlorophenyl)(1H-imidazol- 1-yl)methyl]phenyl]acetamide (interm. 47).

c) A mixture of 80 parts of intermediate 47, namely N-[4-[(3-chlorophenyl) (1H-imidazol- 1-yl)methyl]-phenyl]acetamide, 150 ml of an aqueous hydrochloric acid solution 2N and 15.8 parts of methanol was stirred for 2 hours at reflux temperature. The reaction mixture was evaporated and the residue was basified. The product was extracted with dichloromethane and the extract was dried, filtered and evaporated. The residue was purified by column chromatography (silica gel; CH$_2$Cl$_2$/CH$_3$OH 98:2). The eluent of the desired fraction was evaporated, yielding 14.1 parts (20.2%) of 4-[(3-chlorophenyl) (1H-imidazol- 1-yl)methyl]benzenamine (interm. 48).

In a similar manner there was also prepared:
4-[(3-fluorophenyl)(1H-imidazol- 1-yl)methyl]benzenamine (interm. 49).

Example 10

To a stirred and cooled (0° C.) mixture of 14.6 parts of 4-[(4-chlorophenyl)(1H-imidazol-1-yl)methyl]benzenamine, 60.9 parts of benzene and 6.86 parts of pyridine was added a solution of 10.6 parts of 3-phenyl-2-propenoyl chloride in 17.4 parts of benzene under a nitrogen atmosphere. After stirring overnight at room temperature, the reaction mixture was basified and extracted with ethyl acetate. The extract was washed with water, dried, filtered and evaporated. The residue was crystallized from dichloromethane. The product was filtered off and dried, yielding 17.7 parts (83.8%) of N-[4-[(4-chlorophenyl) (1H-imidazol-1-yl)methyl]phenyl]3-phenyl-2-propenamide; mp. 244° C. (interm. 50). In a similar manner there were also prepared the intermediates listed in Table 3:

TABLE 3

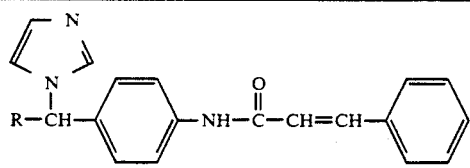

| Int. No. | R | physical data (mp. in °C.) |
|---|---|---|
| 51 | C₆H₅ | — |
| 52 | i.C₃H₇ | 217 |
| 53 | 3-ClC₆H₄ | — |
| 54 | 3-FC₆H₄ | — |
| 55 | 4-FC₆H₄ | — |
| 56 | H | 195 |

EXAMPLE 11

To a stirred solution of 10 parts of 4-[(1H-imidazol-1-yl)methyl]benzenamine in 180 parts of 1,2-dichloroethane were added dropwise 3.9 parts of 4-methylene-2-oxetanone. After stirring for ½ hour at room temperature, the precipitate was filtered off, washed with 1,2-dichloroethane and dried, yielding 9.8 parts (74.8%) of N-[4-(1H-imidazol-1-ylmethyl)phenyl]-3-oxobutanamide; mp. 175° C.(interm. 57). In a similar manner there were also prepared the intermediates listed in Table 4:

TABLE 4

| Int. No. | R | physical data (mp. in °C.) |
|---|---|---|
| 58 | H | — |
| 59 | 4-F | — |
| 60 | 4-Cl | — |
| 61 | 3-Cl | — |
| 62 | 3-F | — |

B. Preparation of the final compounds

Example 12

A mixture of 3.4 parts of 7-[chlorophenylmethyl]quinoline, 4.5 parts of 1H-imidazole and 72 parts of N,N-dimethylformamide was stirred for 6 hours at 80° C. The reaction mixture was evaporated to dry and the residue was taken up in water. The product was extracted three times with 65 parts of dichloromethane. The combined extracts were dried, filtered and evaporated. The residue was purified by column chromatography over silica gel using a mixture of dichloromethane and methanol (95:5 by volume) as eluent. The pure fractions were collected and the eluent was evaporated. The residue was crystallized from a mixture of 2,2'-oxybispropane and 2-propanone. The product was filtered off and dried, yielding 1.27 parts (33.2%) of 7-[(1H-imidazol-1yl)phenylmethyl]quinoline; mp. 110.7° C.(compound 26).

Example 13

A mixture of 12.3 parts of 6-(chloromethyl)quinoline, 9.5 parts of 1H-imidazole, 19.2 parts of potassium carbonate and 135 parts of N,N-dimethylformamide was stirred for 3 hours at 80° C. After evaporation to dry, the residue was taken up in water and further purified according to similar procedures as described in example 12, yielding 10 parts (48%) of 6-(1H-imidazol-1-ylmethyl)quinoline dihydrochloride; mp. 254.6° C. (compound 19).

Example 14

A mixture of 5.34 parts of 6-[chloro(4-chlorophenyl)methyl]quinoline, 6.4 parts of 1H-1,2,4-triazole, 1.26 parts of potassium carbonate and 79 parts of acetonitrile was stirred for 8 hours at reflux temperature. After evaporation to dry, the residue was taken up in water and was further purified according to similar procedures as described in example 12, yielding 3 parts (49.2%) of 6-[(4-chlorophenyl)(4-H-1,2,4-triazol-4-yl)methyl]quinoline hemihydrate; mp. 87.8° C. (compound 35).

Example 15

A mixture of 2.3 parts of 6-(1-chloroethyl)-3,4-dihydro-2(1H)-quinolinone hydrochloride, 24 parts of acetonitrile, 7.7 parts of dimethyl sulfoxide and 3.8 parts of 1H-imidazole was stirred overnight at 60°–70° C. The reaction mixture was poured into water, extracted and further purified according similar procedures as described in example 12, yielding 1.2 parts (53.5%) of 3,4-dihydro-6-[4-(1H-imidazol-1-yl)ethyl]-2(1H)-quinolinone; mp. 184.8° C. (compound 12).

Example 16

A mixture of 15 parts of α-phenyl-6-quinolinemethanol, 21 parts of 1,1'-carbonyl-bis[1H-imidazole] and 135 parts of N,N-dimethylformamide was stirred for 12 hours at room temperature. After evaporation to dry, the residue was stirred for 20 minutes at room temperature in a mixture of 140 parts of 1,1'-oxybisethane and 200 parts of water. The mixture was filtered and the filtrate was extracted with trichloromethane and water. The separated organic phase was dried, filtered and evaporated. The residue was purified by column over silica gel, first using a mixture of dichloromethane and methanol (98:2 by volume) and then a mixture of ethyl acetate and cyclohexane (70:30 by volume) as eluents. The pure fractions were collected and the eluent was evaporated. The residue was converted into the sulfate salt in 8 parts of 2-propanone and ethanol at 0° C. The salt was filtered off and crystallized from a mixture of 2-propanol and methanol. The product was filtered off and dried, yielding 1.33 parts (5.1%) of 6-[(1H-imidazol- 1-yl)phenyl-methyl]quinoline sulfate(1:1), monohydrate; mp. 135° C. (compound 23).

Example 17

7 Parts of N-[4-(1H-imidazol-1-ylmethyl)phenyl]-3-oxobutanamide were added dropwise to 73.6 parts of concentrated sulfuric acid (exothermic reaction, the temperature rose to 90° C.). Upon complete addition, the mixture was stirred for 1 hour at 70° C. The reaction mixture was poured into crushed ice and the whole was neutralized with an ammonium hydroxide solution to pH 9. The precipitated product was filtered off and taken up in water. The whole was extracted with dichloromethane. The aqueous layer was concentrated. The crystallized product was filtered off, washed with 2-propanone and dried in vacuo at 100° C., yielding 2.25 parts (34.8%) of 6-(1H-imidazol-1-ylmethyl)-4-methyl-2(1H)-quinolinone; mp. 266.0° C. (compound 1).

Example 18

To a stirred and heated (100° C.) solution of 10 parts of 4-(1H-imidazol-1-ylmethyl)benzenamine in 50 parts of polyphosphoric acid were added 15 parts of ethyl 3-oxobutanoate. The whole was stirred for 4 hours at 140° C. 100 Parts of water were added to the mixture and the whole was neutralized with potassium carbonate. The product was extracted with a mixture of ethyl acetate and methanol. The extract was dried, filtered and concentrated. The concentrate was crystallized from a mixture of 2-propanone and methanol. The product was filtered off and dried, yielding 2 parts (14.4%) of 6-(1H-imidazol-1-ylmethyl)-2-methyl-4(1H)quinolinone; mp. 245.5° C. (decomp.) (compound 51).

Example 19

To a stirred solution of 10.5 parts of N-[4-(1H-imidazol-1yl)phenylmethyl]phenyl]-3-phenyl-2-propenamide in 110 parts of chlorobenzene were added 18.5 parts of aluminium chloride. The reaction mixture was stirred for 3 hours at 120° C. After cooling to room temperature, the product was extracted with ethyl acetate. The extract was dried, filtered and evaporated. The residue was purified by column chromatography over silica gel using a mixture of dichloromethane and methanol (90:10 by volume) as eluent. The pure fractions were collected and the eluent was evaporated. The residue was crystallized from a mixture of 2-propanone and methanol. The product was filtered off and dried, yielding 1.3 parts (15.4%) of 6-[(1H-imidazol-1-yl)phenylmethyl]-2(1H)-quinolinone; mp. 226.9° C. (compound 2).

Example 20

To a stirred solution of 2 parts of sodium in 24 parts of 1-propanol was added a solution of 5.2 parts of 2-chloro-6-(1H-imidazol-1-ylmethyl)-4-methylquinoline in 16 parts of 1-propanol at room temperature under nitrogen atmosphere. After stirring for 2 hours at reflux temperature, the mixture was evaporated. The residue was taken up in a potassium carbonate solution and the product was extracted with ethyl acetate. The extract was dried, filtered and evaporated. The residue was purified by column chromatography over silica gel using a mixture of dichloromethane and methanol (98:2 by volume) as eluent. The pure fractions were collected and the eluent was evaporated. The residue was crystallized from 2-propanone. The product was filtered off and dried, yielding 1.8 parts (31.9%) of 6-(1H-imidazol-1-ylmethyl)-4-methyl-2-propoxyquinoline; mp. 137.9° C. (compound 25).

Example 21

A solution of 13 parts of 6-(1H-imidazol-1-ylmethyl)-4-methyl-2(1H)-quinolinone in 55 parts of phosphoryl chloride was stirred for 1 hour at room temperature. After evaporation, the residue was purified by column chromatography over silica gel using a mixture of trichloromethane and methanol (95:5 by volume) as eluent. The pure fractions were collected and the eluent was evaporated. The residue was crystallized from a mixture of acetonitrile and 2,2'-oxybispropane. The product was filtered off and dried, yielding 1.75 parts (12.5%) of 2-chloro-6-(1H-imidazol-1-ylmethyl)-4-methylquinoline; mp. 120.6° C. (compound 24).

All the other compounds listed in tables 5 - 9 were obtained by analogous methods of preparation as described in examples 12 - 21, the actual method of preparation being indicated in column 2 (Ex. No.).

TABLE 5

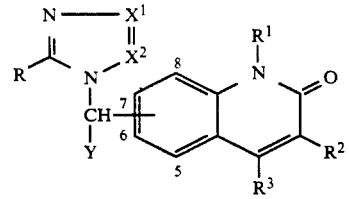

| Comp. No. | Ex. No. | R | X¹=X² | Y | p | R¹ | R² | R³ | mp./salt |
|---|---|---|---|---|---|---|---|---|---|
| 1 | 17 | H | —CH=CH— | H— | 6 | H— | H— | —CH₃ | 266.0 |
| 2 | 19 | H | —CH=CH— | C₆H₅— | 6 | H— | H— | —H | 226.9 |
| 3 | 17 | H | —CH=CH— | C₆H₅— | 6 | H— | H— | —CH₃ | 209.3 |
| 4 | 17 | H | —CH=CH— | 4-F—C₆H₄— | 6 | H— | H— | —CH₃ | 215.6 |
| 5 | 17 | H | —CH=CH— | 4-Cl—C₆H₄— | 6 | H— | H— | —CH₃ | 137.6/0.5H₂O |
| 6 | 17 | H | —CH=CH— | 3-Cl—C₆H₄— | 6 | H— | H— | —CH₃ | 164.3/0.5H₂O |
| 7 | 17 | H | —CH=CH— | 3-F—C₆H₄— | 6 | H— | H— | —CH₃ | 192.9 |
| 8 | 19 | H | —CH=CH— | i-C₃H₇— | 6 | H— | H— | —H | 165.7 |
| 9 | 19 | H | —CH=CH— | 4-Cl—C₆H₄— | 6 | H— | H— | —H | 180.1 |
| 10 | 19 | H | —CH=CH— | 3-Cl—C₆H₄— | 6 | H— | H— | —H | 212.2 |
| 11 | 19 | H | —CH=CH— | 3-F—C₆H₄— | 6 | H— | H— | —H | 210.6 |
| 12 | 19 | H | —CH=CH— | 4-F—C₆H₄— | 6 | H— | H— | —H | 253.7 |
| 13 | 14 | H | —N=CH— | H— | 6 | H— | H— | —H | >300/H₂O |

TABLE 5-continued

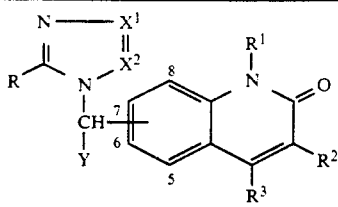

| Comp. No. | Ex. No. | R | X¹=X² | Y | p | R¹ | R² | R³ | mp./salt |
|---|---|---|---|---|---|---|---|---|---|
| 14 | 19 | H | —CH=CH— | H— | 6 | H— | H— | —H | 229.6 |

In the previous and following tables p indicates the position of the 1H-azol-1-yl-methyl moiety on the quinoline ring.

TABLE 6

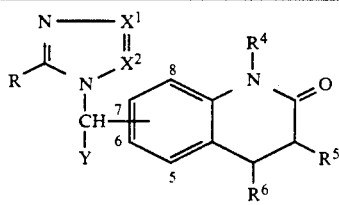

| Comp. No. | Ex. No. | R | —X¹=X²— | Y | p | R⁴ | R⁵ | R⁶ | mp./salt |
|---|---|---|---|---|---|---|---|---|---|
| 15 | 15 | H | —CH=N— | $C_6H_5$— | 6 | H— | H— | H— | 220.1 |
| 16 | 15 | H | —CH=CH— | $C_6H_5$— | 6 | H— | H— | H— | 223.9 |
| 17 | 15 | H | —N=CH— | $C_6H_5$— | 6 | H— | H— | H— | 187.8 |
| 18 | 15 | H | —N=CH— | 3-Cl—$C_6H_4$— | 6 | H— | H— | H— | 170.6/$HNO_3$ |
| 19 | 15 | H | —CH=N— | 3-Cl—$C_6H_4$— | 6 | H— | H— | H— | 110.1/$HNO_3$ |
| 20 | 15 | H | —CH=CH— | 3-Cl—$C_6H_4$— | 6 | H— | H— | H— | 189.5 |
| 21 | 15 | H | —CH=CH— | —$CH_3$ | 6 | H— | H— | H— | 184.8 |
| 22 | 15 | H | —CH=N— | —$CH_3$ | 6 | H— | H— | H— | 172.3 |
| 23 | 15 | H | —N=CH— | —$CH_3$ | 6 | H— | H— | H— | 220.3 |
| 24 | 16 | H | —CH=CH— | c-$C_3H_5$— | 6 | H— | H— | H— | 168.7 |
| 25 | — | H | —CH=CH— | i.$C_3H_7$— | 6 | H— | H— | H— | — |
| 26 | — | H | —N=CH— | i.$C_3H_7$— | 6 | H— | H— | H— | — |
| 27 | — | H | —CH=N— | i.$C_3H_7$— | 6 | H— | H— | H— | — |
| 28 | — | H | —CH=CH— | 3-Cl—$C_6H_4$— | 6 | H— | $CH_3$— | $CH_3$— | — |

TABLE 7

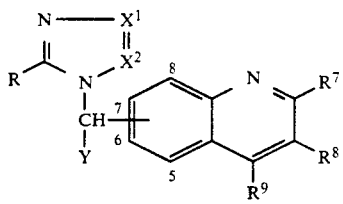

| Comp. No. | Ex. No. | R | —X¹=X² | Y | p | R⁷ | R⁸ | R⁹ | mp./salt |
|---|---|---|---|---|---|---|---|---|---|
| 29 | 13 | H | —CH=CH— | —H | 6 | H | H | H | 254.6/2HCl |
| 30 | 13 | H | —CH=CH— | —H | 8 | H | H | H | 167.8/$(COOH)_2$ |
| 31 | 13 | H | —CH=CH— | —H | 7 | H | H | H | 163.8/2$(COOH)_2$ |
| 32 | 13 | H | —CH=CH— | —H | 5 | H | H | H | 216.4/0.5$(COOH)_2$ |
| 33 | 16 | H | —CH=CH— | $C_6H_5$— | 6 | H | H | H | 79.8/$H_2SO_4$/$H_2O$ |
| 34 | 21 | H | —CH=CH— | —H | 6 | Cl— | H | $CH_3$ | 120.6 |
| 35 | 20 | H | —CH=CH— | —H | 6 | $C_3H_7$—O— | H | $CH_3$ | 137.9 |
| 36 | 12 | H | —CH=CH— | $C_6H_5$— | 7 | H | H | H | 110.7 |
| 37 | 20 | H | —CH=CH— | —H | 6 | i-$C_3H_7$—O— | H | $CH_3$— | 111.1 |
| 38 | 20 | H | —CH=CH— | —H | 6 | $CH_3$—O— | H | $CH_3$— | 142.6 |
| 39 | 21 | H | —CH=CH— | —H | 6 | $CH_3$— | H | Cl— | 103.7 |
| 40 | 20 | H | —CH=CH— | —H | 6 | $CH_3$— | H | $CH_3O$— | 116.9 |
| 41 | 14 | H | —CH=CH— | 3-Cl—$C_6H_4$— | 6 | H | H | H | 120.7 |
| 42 | 14 | H | —CH=CH— | 3-F—$C_6H_4$— | 6 | H | H | H | 98.9 |
| 43 | 14 | H | —N=CH— | $C_6H_5$— | 6 | H | H | H | 173.2 |
| 44 | 14 | H | —CH=N— | $C_6H_5$— | 6 | H | H | H | 115.0/$H_2O$/HCl |
| 45 | 14 | H | —N=CH— | 4-Cl—$C_6H_4$— | 6 | H | H | H | 87.8/0.5$H_2O$ |
| 46 | 14 | H | —CH=N— | 3-Cl—$C_6H_4$— | 6 | H | H | H | 120.7 |
| 47 | 14 | H | —CH=CH— | 3-$CH_3$—$C_6H_4$— | 6 | H | H | H | 124.7 |

TABLE 7-continued

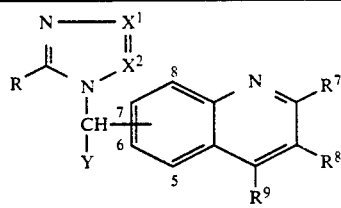

| Comp. No. | Ex. No. | R | $-X^1=X^2$ | Y | p | $R^7$ | $R^8$ | $R^9$ | mp./salt |
|---|---|---|---|---|---|---|---|---|---|
| 48 | 14 | H | —CH=N— | 4-Cl—$C_6H_4$— | 6 | H | H | H | 201.8/HCl/0.5$H_2O$ |
| 49 | 14 | H | —CH=CH— | 3-$CH_3O$—$C_6H_4$— | 6 | H | H | H | 121.3 |
| 50 | 14 | H | —N=CH— | 3-Cl—$C_6H_4$— | 6 | H | H | H | 161.1 |
| 51 | 14 | H | —CH=CH— | 3,4-$F_2$—$C_6H_3$— | 6 | H | H | H | 108.5 |
| 52 | 14 | H | —CH=CH— | 3,4-$(CH_3)_2$—$C_6H_3$— | 6 | H | H | H | 122.1 |
| 53 | 14 | H | —CH=N— | 3,4-$(CH_3)_2$—$C_6H_3$— | 6 | H | H | H | 127.5 |
| 54 | 16 | H | —CH=CH— | 1H-imidazol-1-yl | 6 | H | H | H | 193.8/* |
| 55 | 16 | H | —CH=CH— | 2-thienyl | 6 | H | H | H | 124.7 |
| 56 | 14 | H | —CH=CH— | 3-$CF_3$—$C_6H_4$— | 6 | H | H | H | 133.9 |
| 57 | 14 | H | —CH=CH— | 4-$CH_3$—$C_6H_4$— | 6 | H | H | H | 133.9/* |
| 58 | 14 | H | —N=CH— | 3-F—$C_6H_4$— | 6 | H | H | H | 165.0 |
| 59 | 14 | H | —CH=N— | 3,4-$F_2$—$C_6H_3$— | 6 | H | H | H | 104.2 |
| 60 | 14 | H | —CH=N— | 4-F—$C_6H_4$— | 6 | H | H | H | 135.1/* |
| 61 | 14 | H | —N=CH— | 3-$CH_3$—$C_6H_4$— | 6 | H | H | H | 118.0 |
| 62 | 14 | H | —CH=N— | 4-$CH_3$—$C_6H_4$— | 6 | H | H | H | 164.5/* |
| 63 | 14 | H | —CH=N— | 4-$OCH_3$—$C_6H_4$— | 6 | H | H | H | 151.1/* |
| 64 | 14 | H | —N=CH— | 3-$OCH_3$—$C_6H_4$— | 6 | H | H | H | 142.0 |
| 65 | 14 | H | —N=CH— | 3,4-$F_2$—$C_6H_3$— | 6 | H | H | H | 149.5 |
| 66 | 14 | H | —CH=N— | 3-$CF_3$—$C_6H_4$— | 6 | H | H | H | 142.9 |
| 67 | 14 | H | —CH=CH— | c.$C_6H_{11}$— | 6 | H | H | H | 285.0/2HCl |
| 68 | 14 | H | —CH=N— | 3-$OCH_3$—$C_6H_4$— | 6 | H | H | H | 150.0/* |
| 69 | 14 | $CH_3$ | —CH=CH— | $C_6H_5$— | 6 | H | H | H | 52.6/0.5$H_2O$ |
| 70 | 14 | H | —CH=N— | 3-$CH_3$—$C_6H_4$— | 6 | H | H | H | 117.9 |
| 71 | — | H | —CH=CH— | c.$C_3H_5$— | 6 | H | H | H | — |
| 72 | — | H | —CH=CH— | $CH_3$—C≡C— | 6 | H | H | H | — |
| 73 | — | H | —CH=CH— | $CH_3$—CH=CH— | 6 | H | H | H | — |
| 74 | — | H | —CH=CH— | 3-pyridinyl | 6 | H | H | H | — |
| 75 | — | H | —CH=N— | 3,4$Cl_2$—$C_6H_3$— | 6 | H | H | H | — |
| 76 | — | H | —CH=CH— | 3,4$Cl_2$—$C_6H_3$— | 6 | H | H | H | — |

* = $(COOH)_2$

TABLE 8

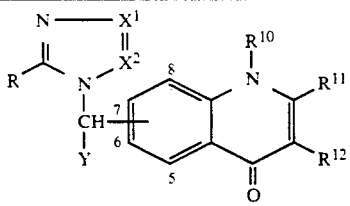

| Comp. No. | Ex. No. | R | $-X^1=X^2-$ | Y | p | $R^{10}$ | $R^{11}$ | $R^{12}$ | mp./salt |
|---|---|---|---|---|---|---|---|---|---|
| 77 | 18 | H | —CH=CH— | —H | 6 | H | —$CH_3$ | —H— | 245.5 (decomp) |

C. Pharmacological Examples

The useful pharmacological properties of the compounds of the present invention can for example be demonstrated by the following experiment.

Example 22

Metabolism of Exogenously Administered All-Trans-Retinoic Acid

Male Wistar rats weighing 200–210 g were orally treated with vehicle (PEG 200) or with 40 mg/kg of a compound of formula (I). One hour later, the animals were anesthetized with ether and injected intrajugularly with 0.50 ml saline solution containing 20 μg of all-trans-retinoic acid. Two hours after this injection, rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehicle-pretreated animals were not detectable (<0.5 ng/ml), whereas compound nos. 2, 3, 4, 5, 6, 7, 8, 9, 10, 11, 12, 15, 16, 20, 21, 24, 33, 41, 42, 55 and 67 enhanced the recovery of all-trans-retinoic acid from the plasma to at last 10 ng/ml after dosing with 40 mg/kg.

Example 23

Metabolism of Endogenously Administered All-Trans-Retinoic Acid

Male Wistar rats weighing 200~210 g were orally treated with vehicle (PEG 200) or with 40 mg/kg of a compound of formula (I). Two hours after drug administration, the rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehicle-pretreated animals were not detectable (<0.5 ng/ml), whereas compound nos. 2, 3, 4, 7, 8, 11, 12, 16, 19, 20, 24, 33, 41, 42, 46, 48, 49, 51, 55, 56, 59, 60, 66, 67, 68, 69 and 70 enhanced the recovery of all-trans-retinoic acid from the plasma to at least 1 ng/ml.

We claim:

1. A compound of the formula:

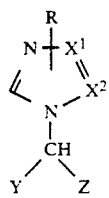
(I)

a pharmaceutically acceptable acid addition salt thereof or a stereochemically isomeric form thereof, wherein:

—$X^1$=$X^2$— represents a bivalent radical of formula

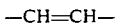 —CH=CH— (x),

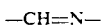 —CH=N— (y), or

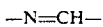 —N=CH— (z):

R represents hydrogen or $C_{1-6}$alkyl;

Y represents hydrogen, $C_{1-10}$alkyl, $C_{3-7}$cycloalkyl, $Ar^1$, $Ar^2$—$C_{1-6}$alkyl, $C_{2-6}$alkenyl or $C_{2-6}$alkynyl; and Z represents a radical of the formula:

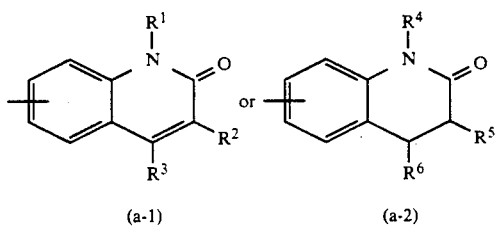

wherein:

$R^1$ and $R^4$ each independently represent hydrogen, $C_{1-6}$alkyl or $Ar^2C_{1-6}$alkyl;

$R^2$ and $R^5$ each independently represent hydrogen, $C_{1-6}$alkyl or $Ar^2$; and $R^3$ and $R^6$ each independently represent hydrogen or $C_{1-6}$alkyl, and wherein in the foregoing:

$Ar^1$ represents phenyl, substituted phenyl, naphthalenyl, pyridinyl, imidazolyl, triazolyl, thienyl, furanyl or thiazolyl, and $Ar^2$ represents phenyl or substituted phenyl, wherein said substituted phenyl in $Ar^1$ or $Ar^2$ represents phenyl substituted with 1, 2 or 3 substituents each independently selected from the group consisting of halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl, provided that:

when (1) —$X^1$=$X^2$—represents a bivalent radical of formula —CH=CH—, (2) R represents hydrogen, and (3) $R^1$, $R^2$, $R^3$, $R^4$, $R^5$ and $R^6$ all represent hydrogen, then Y is other than hydrogen, $C_{1-10}$alkyl, $Ar^1$ or $Ar^2C_{1-6}$alkyl.

2. A compound according to claim 1 wherein R is hydrogen or $C_{1-4}$alkyl; Y is hydrogen, $C_{1-6}$alkyl, $C_{3-7}$cycloalkyl, phenyl, substituted phenyl, pyridinyl, imidazolyl or thienyl and $R^1$, $R^2$, $R^3$, $R^4$, $R^5$ and $R^6$ each independently are hydrogen or $C_{1-4}$alkyl.

3. A compound according to claim 2 wherein —$X^1$=$X^2$— is a radical of formula (x) or (y); and Y is hydrogen, $C_{1-4}$alkyl, cyclopropyl, cyclopentyl, cyclohexyl, imidazolyl, pyridinyl, thienyl or phenyl optionally substituted with one or two substituents each independently selected from halo, $C_{1-4}$alkyl, $C_{1-4}$alkyloxy and trifluoromethyl.

4. A compound according to claim 3 wherein:

Z is a radical of formula (a-1) wherein $R^1$ and $R^2$ are hydrogen, $R^3$ is hydrogen or $C_{1-4}$alkyl and Y is hydrogen, $C_{1-4}$alkyl or phenyl optionally substituted with one or two halo atoms; or Z is a radical of formula (a-2) wherein $R^4$, $R^5$ and $R^6$ all are hydrogen, and Y is hydrogen, $C_{1-4}$alkyl, cyclopropyl or phenyl optionally substituted with one or two halo atoms.

5. A compound according to claim 1 wherein Z is a radical of formula (a-1); R is hydrogen; —$X^1$=$X^2$— is a radical of formula (x) or (y); Y is isopropyl, phenyl or halophenyl; $R^1$ and $R^2$ are both hydrogen; and $R^3$ is methyl.

6. A compound according to claim 1 wherein Z is a radical of formula (a-2); R is hydrogen; —$X^1$=$X^2$— is a radical of formula (x) or (y); Y is cyclopropyl, phenyl or halophenyl; and $R^4$, $R^5$ and $R^6$ are all hydrogen.

7. A compound according to claim 1 wherein the compound is 6-[(4-fluorophenyl) (1H-imidazol-1-yl)methyl]-2(1H)-quinolinone, a pharmaceutically acceptable acid addition salts or a possible stereoisomeric form thereof.

8. A compound according to claim 1 wherein the compound is 6-[(3-chlorophenyl) (1H-imidazol-1-yl)methyl]-3,4-dihydro-2(1H)-quinolinone, a pharmaceutically acceptable acid addition salt or a possible stereoisomer thereof.

9. A compound according to claim 1 wherein the compound is 3,4-dihydro-6-[(1H-imidazol-1-yl)phenylmethyl]-2(1H)-quinolinone, a pharmaceutically acceptable acid addition salt or a possible stereoisomer thereof.

10. A composition comprising an inert carrier and, if desired, other additives, and as active ingredient an effective amount of a compound of the formula:

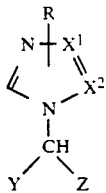 (I)

a pharmaceutically acceptable acid addition salt thereof or a stereochemically isomeric form thereof, wherein:

—$X^1$=$X^2$— represents a bivalent radical of formula

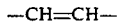 (x),

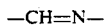 (y), or

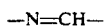 (z);

R represents hydrogen or $C_{1-6}$alkyl;

Y represents hydrogen, $C_{1-10}$alkyl, $C_{3-7}$cycloalkyl, $Ar^1$, $Ar^2$—$C_{1-6}$alkyl, $C_{2-6}$alkenyl or $C_{2-6}$alkynyl; and Z represents a radical of the formula:

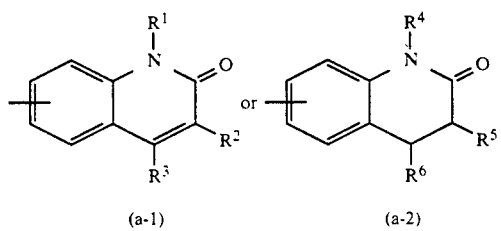

wherein:

$R^1$ and $R^4$ each independently represent hydrogen, $C_{1-6}$alkyl or $Ar^2C_{1-6}$alkyl;

$R^2$ and $R^5$ each independently represent hydrogen, $C_{1-6}$alkyl or $Ar^2$; and $R^3$ and $R^5$ independently represent hydrogen or $C_{1-6}$alkyl, and wherein in the foregoing:

$Ar^1$ represents phenyl, substituted phenyl, naphthalenyl, pyridinyl, imidazolyl, triazolyl, thienyl, furanyl or thiazolyl, and $Ar^2$ represents phenyl or substituted phenyl, wherein said substituted phenyl in $Ar^1$ or $Ar^2$ represents phenyl substituted with 1, 2 or 3 substituents each independently selected from the group consisting of halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl, provided that:
when (1) —$X^1$=$X^2$— represents a bivalent radical of formula —CH=CH—, (2) R represents hydrogen, and (3) $R^1$, $R^2$, $R^3$, $R^4$, $R^5$ and $R^6$ all represent hydrogen, then Y is other than hydrogen, $C_{1-10}$alkyl, $Ar^1$or $Ar^2C_{1-6}$alkyl.

11. A composition according to claim 10 wherein R is hydrogen or $C_{1-4}$alkyl; Y is hydrogen, $C_{1-6}$alkyl, $C_{3-7}$cycloalkyl, phenyl, substituted phenyl, pyridinyl, imidazolyl or thienyl and $R^1$, $R^2$, $R^3$, $R^4$, $R^5$ and $R^6$ each independently are hydrogen or $C_{1-4}$alkyl.

12. A composition according to claim 11 wherein —$X^1$=$X^2$— is a radical of formula (x) or (y); and Y is hydrogen, $C_{1-4}$alkyl, cyclopropyl, cyclopentyl, cyclohexyl, imidazolyl, pyridinyl, thienyl or phenyl optionally substituted with one or two substituents each independently selected from halo, $C_{1-4}$alkyl, $C_{1-4}$alkyloxy and trifluoromethyl.

13. A composition according to claim 12 wherein:
Z is a radical of formula (a-1) wherein $R^1$ and $R^2$ are hydrogen, $R^3$ is hydrogen or $C_{1-4}$alkyl and Y is hydrogen, $C_{1-4}$alkyl or phenyl optionally substituted with one or two halo atoms; or
Z is a radical of formula (a-2) wherein $R^4$, $R^5$ and $R^6$ all are hydrogen, and Y is hydrogen, $C_{1-4}$alkyl, cyclopropyl or phenyl optionally substituted with one or two halo atoms.

14. A composition according to claim 10 wherein Z is a radical of formula (a-1); R is hydrogen; —$X^1$=$X^2$— is a radical of formula (x) or (y); Y is isopropyl, phenyl or halophenyl; $R^1$ and $R^2$ are both hydrogen; and $R^3$ is methyl.

15. A composition according to claim 10 wherein Z is a radical of formula (a-2); R is hydrogen; —$X^1$=$X^2$— is a radical of formula (x) or (y); Y is cyclopropyl, phenyl or halophenyl; and $R^4$, $R^5$ and $R^6$ are all hydrogen.

16. A composition according to claim 10 wherein the compound is 6-[(4-fluorophenyl) (1H-imidazol-1-yl)methyl]-2(1H)-quinolinone, a pharmaceutically acceptable acid addition salts or a possible stereoisomeric form thereof.

17. A composition according to claim 10 wherein the compound is 6-[(3-chlorophenyl) (1H-imidazol-1-yl)methyl]-3,4-dihydro-2(1H)-quinolinone, a pharmaceutically acceptable acid addition salt or a possible stereoisomer thereof.

18. A composition according to claim 10 wherein the compound is 3,4-dihydro-6-[(1H-imidazol-1-yl)phenylmethyl]-2(1H)-quinolinone, a pharmaceutically acceptable acid addition salt or a possible stereoisomer thereof.

* * * * *